(12) United States Patent
Bourdoulous et al.

(10) Patent No.: US 9,127,077 B2
(45) Date of Patent: Sep. 8, 2015

(54) POLYPEPTIDES AND NUCLEIC ACIDS FOR TREATING ERBB2-DEPENDENT CANCERS

(75) Inventors: Sandrine Bourdoulous, Paris (FR); Rym Djerbi-Bouillie, Issy-les-Moulineaux (FR)

(73) Assignee: L'Universite Paris Descartes, Paris (FR)

( * ) Notice: Subject to any disclaimer, the term of this patent is extended or adjusted under 35 U.S.C. 154(b) by 0 days.

(21) Appl. No.: 13/497,924

(22) PCT Filed: Sep. 23, 2010

(86) PCT No.: PCT/EP2010/064055
§ 371 (c)(1),
(2), (4) Date: May 9, 2012

(87) PCT Pub. No.: WO2011/036211
PCT Pub. Date: Mar. 31, 2011

(65) Prior Publication Data
US 2012/0214744 A1   Aug. 23, 2012

(30) Foreign Application Priority Data

Sep. 23, 2009 (EP) .................................. 09305884

(51) Int. Cl.
*A61K 38/17* (2006.01)
*C07K 14/47* (2006.01)
*C07K 14/52* (2006.01)

(52) U.S. Cl.
CPC .................. *C07K 14/47* (2013.01); *C07K 14/52* (2013.01); *C07K 2319/00* (2013.01)

(58) Field of Classification Search
CPC ............... C12Q 1/6886; C12Q 1/6883; A61K 2300/00; C07K 14/47
See application file for complete search history.

(56) References Cited

U.S. PATENT DOCUMENTS

2004/0105860 A1 * 6/2004 Losordo et al. ............ 424/145.1
2006/0228357 A1 * 10/2006 Chang et al. ............... 424/144.1

FOREIGN PATENT DOCUMENTS

| WO | 99/47150 A2 | 9/1999 |
| WO | 2005/014637 A1 | 2/2005 |
| WO | 2008/122789 A2 | 10/2008 |

OTHER PUBLICATIONS

Cha et al, Mol Biol Cell, 2006, 17:2661-2673.*
Burgess et al (J Cell Biol, 1990, 111:2129-2138).*
Lazar et al (Mol Cell Biol, 1998, 8:1247-1252).*
Credo Reference, 2005.*
Bashour et al (Mol and Cell Biol, 2002, 22:1150-1157).*
Elliott et al (Breast Cancer Res, 2004, 7:R365-R373).*
Mangeat et al (Trends in Cell Biol, 1999, 9:187-192).*
Rothe et al (Curr Protoc Protein Sci, 2008, 54:18.11.1-18.11.29).*
Sarrio et al (Breast Cancer Res and Treat, 2006, 98:71-79).*
Ghatak et al (Journal of Biological Chemistry, 280:8875-8883).*
Shattuck et al (Cancer Research, 2008, 68:1471-477).*
Tolgay et al (Cancer, 2003, 97:1841-1848).*
Adams et al., Cancer Immunology Immunotherapy, 2006, 55:717-727.*
Hughes et al., Molecular Cancer Therapeutics, 2009, 8(7)1885-1892.*
Ju et al.; "Akt1 Governs Breast Cancer Progression In Vivo"; Proceedings of the National Academy of Sciences of the United States of America, vol. 104, No. 18, May 1, 2007, pp. 7438-7443.
Hoffmann et al.; "Activation of ErbB2 Receptor Tyrosine Kinase Supports Invation of Endothelial Cells by *Neisseria meningitidis*"; The Journal of Cell Biology, vol. 155, No. 1, Oct. 1, 2001, pp. 133-143.

* cited by examiner

*Primary Examiner* — Sean Aeder
*Assistant Examiner* — Julie Wu
(74) *Attorney, Agent, or Firm* — Whitham Curtis Christofferson & Cook, PC

(57) ABSTRACT

The present invention relates to polypeptides, nucleic acids and pharmaceutical compositions suitable for use in the treatment of ErbB2 dependent-cancers, in particular of tumors overexpressing ErbB2 or expressing mutated forms of the ErbB2 gene.

5 Claims, 8 Drawing Sheets

SEQUENCE LISTING

```
<160> NUMBER OF SEQ ID NOS: 22

<210> SEQ ID NO 1
<211> LENGTH: 295
<212> TYPE: PRT
<213> ORGANISM: Homo sapiens

<400> SEQUENCE: 1

Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Tyr Phe Gly Leu His
        35                  40                  45

Tyr Val Asp Asn Lys Gly Phe Pro Thr Trp Leu Lys Leu Asp Lys Lys
50                  55                  60

Val Ser Ala Gln Glu Val Arg Lys Glu Asn Pro Leu Gln Phe Lys Phe
65                  70                  75                  80

Arg Ala Lys Phe Tyr Pro Glu Asp Val Ala Glu Glu Leu Ile Gln Asp
                85                  90                  95

Ile Thr Gln Lys Leu Phe Phe Leu Gln Val Lys Glu Gly Ile Leu Ser
            100                 105                 110

Asp Glu Ile Tyr Cys Pro Pro Glu Thr Ala Val Leu Leu Gly Ser Tyr
        115                 120                 125

Ala Val Gln Ala Lys Phe Gly Asp Tyr Asn Lys Glu Val His Lys Ser
    130                 135                 140

Gly Tyr Leu Ser Ser Glu Arg Leu Ile Pro Gln Arg Val Met Asp Gln
145                 150                 155                 160

His Lys Leu Thr Arg Asp Gln Trp Glu Asp Arg Ile Gln Val Trp His
                165                 170                 175

Ala Glu His Arg Gly Met Leu Lys Asp Asn Ala Met Leu Glu Tyr Leu
            180                 185                 190

Lys Ile Ala Gln Asp Leu Glu Met Tyr Gly Ile Asn Tyr Phe Glu Ile
        195                 200                 205

Lys Asn Lys Lys Gly Thr Asp Leu Trp Leu Gly Val Asp Ala Leu Gly
    210                 215                 220

Leu Asn Ile Tyr Glu Lys Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                245                 250                 255
```

Ile Lys Pro Ile Asp Lys Lys Ala Pro Asp Phe Val Phe Tyr Ala Pro
            260                 265                 270

Arg Leu Arg Ile Asn Lys Arg Ile Leu Gln Leu Cys Met Gly Asn His
            275                 280                 285

Glu Leu Tyr Met Arg Arg Arg
            290                 295

<210> SEQ ID NO 2
<211> LENGTH: 295
<212> TYPE: PRT
<213> ORGANISM: Homo sapiens

<400> SEQUENCE: 2

Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Phe Phe Gly Leu Gln
        35                  40                  45

Tyr Gln Asp Thr Lys Gly Phe Ser Thr Trp Leu Lys Leu Asn Lys Lys
    50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Glu Leu Ile Gln Asp
                85                  90                  95

Ile Thr Gln Arg Leu Phe Phe Leu Gln Val Lys Glu Gly Ile Leu Asn
            100                 105                 110

Asp Asp Ile Tyr Cys Pro Pro Glu Thr Ala Val Leu Leu Ala Ser Tyr
        115                 120                 125

Ala Val Gln Ser Lys Tyr Gly Asp Phe Asn Lys Glu Val His Lys Ser
    130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175

Glu Glu His Arg Gly Met Leu Arg Glu Asp Ala Val Leu Glu Tyr Leu
            180                 185                 190

Lys Ile Ala Gln Asp Leu Glu Met Tyr Gly Val Asn Tyr Phe Ser Ile
        195                 200                 205

Lys Asn Lys Lys Gly Ser Glu Leu Trp Leu Gly Val Asp Ala Leu Gly
    210                 215                 220

Leu Asn Ile Tyr Glu Gln Asn Asp Arg Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Ala Leu Cys Met Gly Asn His
            275                 280                 285

Glu Leu Tyr Met Arg Arg Arg
            290                 295

<210> SEQ ID NO 3
<211> LENGTH: 295
<212> TYPE: PRT
<213> ORGANISM: Homo sapiens

<400> SEQUENCE: 3

```
Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Val Gly Leu Arg Glu Val Trp Phe Phe Gly Leu Gln
        35                  40                  45

Tyr Val Asp Ser Lys Gly Tyr Ser Thr Trp Leu Lys Leu Asn Lys Lys
    50                  55                  60

Val Thr Gln Gln Asp Val Lys Lys Glu Asn Pro Leu Gln Phe Lys Phe
65                  70                  75                  80

Arg Ala Lys Phe Phe Pro Glu Asp Val Ser Glu Glu Leu Ile Gln Glu
                85                  90                  95

Ile Thr Gln Arg Leu Phe Phe Leu Gln Val Lys Glu Ala Ile Leu Asn
            100                 105                 110

Asp Glu Ile Tyr Cys Pro Pro Glu Thr Ala Val Leu Leu Ala Ser Tyr
        115                 120                 125

Ala Val Gln Ala Lys Tyr Gly Asp Tyr Asn Lys Glu Ile His Lys Pro
    130                 135                 140

Gly Tyr Leu Ala Asn Asp Arg Leu Leu Pro Gln Arg Val Leu Glu Gln
145                 150                 155                 160

His Lys Leu Thr Lys Glu Gln Trp Glu Glu Arg Ile Gln Asn Trp His
                165                 170                 175

Glu Glu His Arg Gly Met Leu Arg Glu Asp Ser Met Met Glu Tyr Leu
            180                 185                 190

Lys Ile Ala Gln Asp Leu Glu Met Tyr Gly Val Asn Tyr Phe Glu Ile
        195                 200                 205

Lys Asn Lys Lys Gly Thr Glu Leu Trp Leu Gly Val Asp Ala Leu Gly
    210                 215                 220

Leu Asn Ile Tyr Glu His Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Ala Leu Cys Met Gly Asn His
        275                 280                 285

Glu Leu Tyr Met Arg Arg
    290                 295
```

<210> SEQ ID NO 4
<211> LENGTH: 291
<212> TYPE: PRT
<213> ORGANISM: Homo sapiens

<400> SEQUENCE: 4

```
Thr Phe Thr Val Arg Ile Val Thr Met Asp Ala Glu Met Glu Phe Asn
1               5                   10                  15

Cys Glu Met Lys Trp Lys Gly Lys Asp Leu Phe Asp Leu Val Cys Arg
            20                  25                  30

Thr Leu Gly Leu Arg Glu Thr Trp Phe Phe Gly Leu Gln Tyr Thr Ile
        35                  40                  45

Lys Asp Thr Val Ala Trp Leu Lys Met Asp Lys Lys Val Leu Asp His
    50                  55                  60
```

Asp Val Ser Lys Glu Glu Pro Val Thr Phe His Phe Leu Ala Lys Phe
65                  70                  75                  80

Tyr Pro Glu Asn Ala Glu Glu Leu Val Gln Glu Ile Thr Gln His
                85                  90                  95

Leu Phe Phe Leu Gln Val Lys Lys Gln Ile Leu Asp Glu Lys Ile Tyr
            100                 105                 110

Cys Pro Pro Glu Ala Ser Val Leu Leu Ala Ser Tyr Ala Val Gln Ala
            115                 120                 125

Lys Tyr Gly Asp Tyr Asp Pro Ser Val His Lys Arg Gly Phe Leu Ala
130                 135                 140

Gln Glu Glu Leu Leu Pro Lys Arg Val Ile Asn Leu Tyr Gln Met Thr
145                 150                 155                 160

Pro Glu Met Trp Glu Glu Arg Ile Thr Ala Trp Tyr Ala Glu His Arg
                165                 170                 175

Gly Arg Ala Arg Asp Glu Ala Glu Met Glu Tyr Leu Lys Ile Ala Gln
            180                 185                 190

Asp Leu Glu Met Tyr Gly Val Asn Tyr Phe Ala Ile Arg Asn Lys Lys
            195                 200                 205

Gly Thr Glu Leu Leu Leu Gly Val Asp Ala Leu Gly Leu His Ile Tyr
210                 215                 220

Asp Pro Glu Asn Arg Leu Thr Pro Lys Ile Ser Phe Pro Trp Asn Glu
225                 230                 235                 240

Ile Arg Asn Ile Ser Tyr Ser Asp Lys Glu Phe Thr Ile Lys Pro Leu
                245                 250                 255

Asp Lys Lys Ile Asp Val Phe Lys Phe Asn Ser Ser Lys Leu Arg Val
            260                 265                 270

Asn Lys Leu Ile Leu Gln Leu Cys Ile Gly Asn His Asp Leu Phe Met
            275                 280                 285

Arg Arg Arg
    290

<210> SEQ ID NO 5
<211> LENGTH: 586
<212> TYPE: PRT
<213> ORGANISM: Homo sapiens

<400> SEQUENCE: 5

Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Tyr Phe Gly Leu His
            35                  40                  45

Tyr Val Asp Asn Lys Gly Phe Pro Thr Trp Leu Lys Leu Asp Lys Lys
50                  55                  60

Val Ser Ala Gln Glu Val Arg Lys Glu Asn Pro Leu Gln Phe Lys Phe
65                  70                  75                  80

Arg Ala Lys Phe Tyr Pro Glu Asp Val Ala Glu Glu Leu Ile Gln Asp
                85                  90                  95

Ile Thr Gln Lys Leu Phe Phe Leu Gln Val Lys Glu Gly Ile Leu Ser
            100                 105                 110

Asp Glu Ile Tyr Cys Pro Pro Glu Thr Ala Val Leu Leu Gly Ser Tyr
            115                 120                 125

Ala Val Gln Ala Lys Phe Gly Asp Tyr Asn Lys Glu Val His Lys Ser

```
                130             135             140
Gly Tyr Leu Ser Ser Glu Arg Leu Ile Pro Gln Arg Val Met Asp Gln
145                 150                 155                 160

His Lys Leu Thr Arg Asp Gln Trp Glu Asp Arg Ile Gln Val Trp His
                165                 170                 175

Ala Glu His Arg Gly Met Leu Lys Asp Asn Ala Met Leu Glu Tyr Leu
            180                 185                 190

Lys Ile Ala Gln Asp Leu Glu Met Tyr Gly Ile Asn Tyr Phe Glu Ile
            195                 200                 205

Lys Asn Lys Lys Gly Thr Asp Leu Trp Leu Gly Val Asp Ala Leu Gly
            210                 215                 220

Leu Asn Ile Tyr Glu Lys Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
                260                 265                 270

Arg Leu Arg Ile Asn Lys Arg Ile Leu Gln Leu Cys Met Gly Asn His
                275                 280                 285

Glu Leu Tyr Met Arg Arg Lys Pro Asp Thr Ile Glu Val Gln Gln
290                 295                 300

Met Lys Ala Gln Ala Arg Glu Glu Lys His Gln Lys Gln Leu Glu Arg
305                 310                 315                 320

Gln Gln Leu Glu Thr Glu Lys Lys Arg Glu Thr Val Glu Arg Glu
                325                 330                 335

Lys Glu Gln Met Met Arg Glu Lys Glu Glu Leu Met Leu Arg Leu Gln
                340                 345                 350

Asp Tyr Glu Glu Lys Thr Lys Lys Ala Glu Arg Glu Leu Ser Glu Gln
                355                 360                 365

Ile Gln Arg Ala Leu Gln Leu Glu Glu Glu Arg Lys Arg Ala Gln Glu
            370                 375                 380

Glu Ala Glu Arg Leu Glu Ala Asp Arg Met Ala Ala Leu Arg Ala Lys
385                 390                 395                 400

Glu Glu Leu Glu Arg Gln Ala Val Asp Gln Ile Lys Ser Gln Glu Gln
                405                 410                 415

Leu Ala Ala Glu Leu Ala Glu Tyr Thr Ala Lys Ile Ala Leu Leu Glu
            420                 425                 430

Glu Ala Arg Arg Arg Lys Glu Asp Glu Val Glu Glu Trp Gln His Arg
            435                 440                 445

Ala Lys Glu Ala Gln Asp Asp Leu Val Lys Thr Lys Glu Glu Leu His
450                 455                 460

Leu Val Met Thr Ala Pro Pro Pro Pro Pro Val Tyr Glu Pro
465                 470                 475                 480

Val Ser Tyr His Val Gln Glu Ser Leu Gln Asp Glu Gly Ala Glu Pro
                485                 490                 495

Thr Gly Tyr Ser Ala Glu Leu Ser Ser Glu Gly Ile Arg Asp Asp Arg
                500                 505                 510

Asn Glu Glu Lys Arg Ile Thr Glu Ala Glu Lys Asn Glu Arg Val Gln
            515                 520                 525

Arg Gln Leu Leu Thr Leu Ser Ser Glu Leu Ser Gln Ala Arg Asp Glu
            530                 535                 540

Asn Lys Arg Thr His Asn Asp Ile Ile His Asn Glu Asn Met Arg Gln
545                 550                 555                 560
```

Gly Arg Asp Lys Tyr Lys Thr Leu Arg Gln Ile Arg Gln Gly Asn Thr
                565                 570                 575

Lys Gln Arg Ile Asp Glu Phe Glu Ala Leu
            580                 585

<210> SEQ ID NO 6
<211> LENGTH: 577
<212> TYPE: PRT
<213> ORGANISM: Homo sapiens

<400> SEQUENCE: 6

Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Phe Phe Gly Leu Gln
        35                  40                  45

Tyr Gln Asp Thr Lys Gly Phe Ser Thr Trp Leu Lys Leu Asn Lys Lys
    50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Leu Ile Gln Asp
                85                  90                  95

Ile Thr Gln Arg Leu Phe Phe Leu Gln Val Lys Glu Gly Ile Leu Asn
            100                 105                 110

Asp Asp Ile Tyr Cys Pro Pro Glu Thr Ala Val Leu Leu Ala Ser Tyr
        115                 120                 125

Ala Val Gln Ser Lys Tyr Gly Asp Phe Asn Lys Glu Val His Lys Ser
    130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175

Glu Glu His Arg Gly Met Leu Arg Glu Asp Ala Val Leu Glu Tyr Leu
            180                 185                 190

Lys Ile Ala Gln Asp Leu Glu Met Tyr Gly Val Asn Tyr Phe Ser Ile
        195                 200                 205

Lys Asn Lys Lys Gly Ser Glu Leu Trp Leu Gly Val Asp Ala Leu Gly
    210                 215                 220

Leu Asn Ile Tyr Glu Gln Asn Asp Arg Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Ala Leu Cys Met Gly Asn His
        275                 280                 285

Glu Leu Tyr Met Arg Arg Arg Lys Pro Asp Thr Ile Glu Val Gln Gln
    290                 295                 300

Met Lys Ala Gln Ala Glu Glu Lys His Gln Lys Gln Met Glu Arg
305                 310                 315                 320

Ala Met Leu Glu Asn Glu Lys Lys Arg Glu Met Ala Glu Lys Glu
                325                 330                 335

Lys Glu Lys Ile Glu Arg Glu Lys Glu Glu Leu Met Glu Arg Leu Lys

```
                340                 345                 350
Gln Ile Glu Glu Gln Thr Lys Lys Ala Gln Gln Glu Leu Glu Glu Gln
            355                 360                 365
Thr Arg Arg Ala Leu Glu Leu Glu Gln Glu Arg Lys Arg Ala Gln Ser
        370                 375                 380
Glu Ala Glu Lys Leu Ala Lys Glu Arg Gln Ala Glu Glu Ala Lys
385                 390                 395                 400
Glu Ala Leu Leu Gln Ala Ser Arg Asp Gln Lys Lys Thr Gln Glu Gln
                405                 410                 415
Leu Ala Leu Glu Met Ala Glu Leu Thr Ala Arg Ile Ser Gln Leu Glu
            420                 425                 430
Met Ala Arg Gln Lys Lys Glu Ser Glu Ala Val Glu Trp Gln Gln Lys
        435                 440                 445
Ala Gln Met Val Gln Glu Asp Leu Glu Lys Thr Arg Ala Glu Leu Lys
    450                 455                 460
Thr Ala Met Ser Thr Pro His Val Ala Glu Pro Ala Glu Asn Glu Gln
465                 470                 475                 480
Asp Glu Gln Asp Glu Asn Gly Ala Glu Ala Ser Ala Asp Leu Arg Ala
                485                 490                 495
Asp Ala Met Ala Lys Asp Arg Ser Glu Glu Arg Thr Thr Glu Ala
            500                 505                 510
Glu Lys Asn Glu Arg Val Gln Lys His Leu Lys Ala Leu Thr Ser Glu
        515                 520                 525
Leu Ala Asn Ala Arg Asp Glu Ser Lys Lys Thr Ala Asn Asp Met Ile
    530                 535                 540
His Ala Glu Asn Met Arg Leu Gly Arg Asp Lys Tyr Lys Thr Leu Arg
545                 550                 555                 560
Gln Ile Arg Gln Gly Asn Thr Lys Gln Arg Ile Asp Glu Phe Glu Ser
                565                 570                 575
Met

<210> SEQ ID NO 7
<211> LENGTH: 583
<212> TYPE: PRT
<213> ORGANISM: Homo sapiens

<400> SEQUENCE: 7

Met Pro Lys Pro Ile Asn Val Arg Val Thr Thr Met Asp Ala Glu Leu
1               5                   10                  15
Glu Phe Ala Ile Gln Pro Asn Thr Thr Gly Lys Gln Leu Phe Asp Gln
            20                  25                  30
Val Val Lys Thr Val Gly Leu Arg Glu Val Trp Phe Phe Gly Leu Gln
        35                  40                  45
Tyr Val Asp Ser Lys Gly Tyr Ser Thr Trp Leu Lys Leu Asn Lys Lys
    50                  55                  60
Val Thr Gln Gln Asp Val Lys Lys Glu Asn Pro Leu Gln Phe Lys Phe
65                  70                  75                  80
Arg Ala Lys Phe Phe Pro Glu Asp Val Ser Glu Glu Leu Ile Gln Glu
                85                  90                  95
Ile Thr Gln Arg Leu Phe Phe Leu Gln Val Lys Glu Ala Ile Leu Asn
            100                 105                 110
Asp Glu Ile Tyr Cys Pro Pro Glu Thr Ala Val Leu Leu Ala Ser Tyr
        115                 120                 125
Ala Val Gln Ala Lys Tyr Gly Asp Tyr Asn Lys Glu Ile His Lys Pro
```

```
                    130                 135                 140
Gly Tyr Leu Ala Asn Asp Arg Leu Leu Pro Gln Arg Val Leu Glu Gln
145                 150                 155                 160

His Lys Leu Thr Lys Glu Gln Trp Glu Glu Arg Ile Gln Asn Trp His
                165                 170                 175

Glu Glu His Arg Gly Met Leu Arg Glu Asp Ser Met Met Glu Tyr Leu
            180                 185                 190

Lys Ile Ala Gln Asp Leu Glu Met Tyr Gly Val Asn Tyr Phe Glu Ile
        195                 200                 205

Lys Asn Lys Lys Gly Thr Glu Leu Trp Leu Gly Val Asp Ala Leu Gly
    210                 215                 220

Leu Asn Ile Tyr Glu His Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Ala Leu Cys Met Gly Asn His
        275                 280                 285

Glu Leu Tyr Met Arg Arg Lys Pro Asp Thr Ile Glu Val Gln Gln
    290                 295                 300

Met Lys Ala Gln Ala Arg Glu Lys His Gln Lys Gln Leu Glu Arg
305                 310                 315                 320

Ala Gln Leu Glu Asn Glu Lys Lys Arg Glu Ile Ala Glu Lys Glu
                325                 330                 335

Lys Glu Arg Ile Glu Arg Glu Lys Glu Glu Leu Met Glu Arg Leu Lys
            340                 345                 350

Gln Ile Glu Glu Gln Thr Ile Lys Ala Gln Lys Glu Leu Glu Glu Gln
        355                 360                 365

Thr Arg Lys Ala Leu Glu Leu Asp Gln Glu Arg Lys Arg Ala Lys Glu
    370                 375                 380

Glu Ala Glu Arg Leu Glu Lys Glu Arg Arg Ala Ala Glu Glu Ala Lys
385                 390                 395                 400

Ser Ala Ile Ala Lys Gln Ala Ala Asp Gln Met Lys Asn Gln Glu Gln
                405                 410                 415

Leu Ala Ala Glu Leu Ala Glu Phe Thr Ala Lys Ile Ala Leu Leu Glu
            420                 425                 430

Glu Ala Lys Lys Lys Lys Glu Glu Glu Ala Thr Glu Trp Gln His Lys
        435                 440                 445

Ala Phe Ala Ala Gln Glu Asp Leu Glu Lys Thr Lys Glu Glu Leu Lys
    450                 455                 460

Thr Val Met Ser Ala Pro Pro Pro Pro Pro Pro Val Ile Pro
465                 470                 475                 480

Pro Thr Glu Asn Glu His Asp Glu His Asp Glu Asn Asn Ala Glu Ala
                485                 490                 495

Ser Ala Glu Leu Ser Asn Glu Gly Val Met Asn His Arg Ser Glu Glu
            500                 505                 510

Glu Arg Val Thr Glu Thr Gln Lys Asn Glu Arg Val Lys Lys Gln Leu
        515                 520                 525

Gln Ala Leu Ser Ser Glu Leu Ala Gln Ala Arg Asp Glu Thr Lys Lys
    530                 535                 540

Thr Gln Asn Asp Val Leu His Ala Glu Asn Val Lys Ala Gly Arg Asp
545                 550                 555                 560
```

```
Lys Tyr Lys Thr Leu Arg Gln Ile Arg Gln Gly Asn Thr Lys Gln Arg
                565                 570                 575

Ile Asp Glu Phe Glu Ala Met
            580

<210> SEQ ID NO 8
<211> LENGTH: 595
<212> TYPE: PRT
<213> ORGANISM: Homo sapiens

<400> SEQUENCE: 8

Met Ala Gly Ala Ile Ala Ser Arg Met Ser Phe Ser Ser Leu Lys Arg
1               5                   10                  15

Lys Gln Pro Lys Thr Phe Thr Val Arg Ile Val Thr Met Asp Ala Glu
                20                  25                  30

Met Glu Phe Asn Cys Glu Met Lys Trp Lys Gly Lys Asp Leu Phe Asp
            35                  40                  45

Leu Val Cys Arg Thr Leu Gly Leu Arg Glu Thr Trp Phe Phe Gly Leu
        50                  55                  60

Gln Tyr Thr Ile Lys Asp Thr Val Ala Trp Leu Lys Met Asp Lys Lys
65                  70                  75                  80

Val Leu Asp His Asp Val Ser Lys Glu Glu Pro Val Thr Phe His Phe
                85                  90                  95

Leu Ala Lys Phe Tyr Pro Glu Asn Ala Glu Glu Leu Val Gln Glu
            100                 105                 110

Ile Thr Gln His Leu Phe Phe Leu Gln Val Lys Lys Gln Ile Leu Asp
        115                 120                 125

Glu Lys Ile Tyr Cys Pro Pro Glu Ala Ser Val Leu Leu Ala Ser Tyr
130                 135                 140

Ala Val Gln Ala Lys Tyr Gly Asp Tyr Asp Pro Ser Val His Lys Arg
145                 150                 155                 160

Gly Phe Leu Ala Gln Glu Glu Leu Leu Pro Lys Arg Val Ile Asn Leu
                165                 170                 175

Tyr Gln Met Thr Pro Glu Met Trp Glu Glu Arg Ile Thr Ala Trp Tyr
            180                 185                 190

Ala Glu His Arg Gly Arg Ala Arg Asp Glu Ala Glu Met Glu Tyr Leu
        195                 200                 205

Lys Ile Ala Gln Asp Leu Glu Met Tyr Gly Val Asn Tyr Phe Ala Ile
210                 215                 220

Arg Asn Lys Lys Gly Thr Glu Leu Leu Leu Gly Val Asp Ala Leu Gly
225                 230                 235                 240

Leu His Ile Tyr Asp Pro Glu Asn Arg Leu Thr Pro Lys Ile Ser Phe
                245                 250                 255

Pro Trp Asn Glu Ile Arg Asn Ile Ser Tyr Ser Asp Lys Glu Phe Thr
            260                 265                 270

Ile Lys Pro Leu Asp Lys Lys Ile Asp Val Phe Lys Phe Asn Ser Ser
        275                 280                 285

Lys Leu Arg Val Asn Lys Leu Ile Leu Gln Leu Cys Ile Gly Asn His
    290                 295                 300

Asp Leu Phe Met Arg Arg Arg Lys Ala Asp Ser Leu Glu Val Gln Gln
305                 310                 315                 320

Met Lys Ala Gln Ala Arg Glu Glu Lys Ala Arg Lys Gln Met Glu Arg
                325                 330                 335

Gln Arg Leu Ala Arg Glu Lys Gln Met Arg Glu Glu Ala Glu Arg Thr
```

```
                    340                 345                 350
    Arg Asp Glu Leu Glu Arg Arg Leu Leu Gln Met Lys Glu Glu Ala Thr
                355                 360                 365
    Met Ala Asn Glu Ala Leu Met Arg Ser Glu Glu Thr Ala Asp Leu Leu
                370                 375                 380
    Ala Glu Lys Ala Gln Ile Thr Glu Glu Glu Ala Lys Leu Leu Ala Gln
    385                 390                 395                 400
    Lys Ala Glu Ala Glu Gln Glu Met Gln Arg Ile Lys Ala Thr Ala
                    405                 410                 415
    Ile Arg Thr Glu Glu Glu Lys Arg Leu Met Glu Gln Lys Val Leu Glu
                    420                 425                 430
    Ala Glu Val Leu Ala Leu Lys Met Ala Glu Glu Ser Glu Arg Arg Ala
                435                 440                 445
    Lys Glu Ala Asp Gln Leu Lys Gln Asp Leu Gln Glu Ala Arg Glu Ala
                450                 455                 460
    Glu Arg Arg Ala Lys Gln Lys Leu Leu Glu Ile Ala Thr Lys Pro Thr
    465                 470                 475                 480
    Tyr Pro Pro Met Asn Pro Ile Pro Ala Pro Leu Pro Pro Asp Ile Pro
                    485                 490                 495
    Ser Phe Asn Leu Ile Gly Asp Ser Leu Ser Phe Asp Phe Lys Asp Thr
                500                 505                 510
    Asp Met Lys Arg Leu Ser Met Glu Ile Glu Lys Glu Lys Val Glu Tyr
                515                 520                 525
    Met Glu Lys Ser Lys His Leu Gln Gln Leu Asn Glu Leu Lys Thr
                530                 535                 540
    Glu Ile Glu Ala Leu Lys Leu Lys Glu Arg Glu Thr Ala Leu Asp Ile
    545                 550                 555                 560
    Leu His Asn Glu Asn Ser Asp Arg Gly Gly Ser Ser Lys His Asn Thr
                    565                 570                 575
    Ile Lys Lys Leu Thr Leu Gln Ser Ala Lys Ser Arg Val Ala Phe Phe
                580                 585                 590
    Glu Glu Leu
            595

<210> SEQ ID NO 9
<211> LENGTH: 22
<212> TYPE: PRT
<213> ORGANISM: artificial sequence
<220> FEATURE:
<223> OTHER INFORMATION: peptide

<400> SEQUENCE: 9

Leu Gly Ala Ser Trp His Ala Arg Pro Asp Lys Cys Cys Leu Gly Tyr
1               5                   10                  15

Gln Lys Arg Pro Leu Pro
            20

<210> SEQ ID NO 10
<211> LENGTH: 11
<212> TYPE: PRT
<213> ORGANISM: artificial sequence
<220> FEATURE:
<223> OTHER INFORMATION: peptide

<400> SEQUENCE: 10

Leu Gly Ala Ser Trp His Ala Arg Pro Asp Lys
1               5                   10
```

<210> SEQ ID NO 11
<211> LENGTH: 8
<212> TYPE: PRT
<213> ORGANISM: Artificial Sequence
<220> FEATURE:
<223> OTHER INFORMATION: Flag tag

<400> SEQUENCE: 11

Asp Tyr Lys Asp Asp Asp Asp Lys
1               5

<210> SEQ ID NO 12
<211> LENGTH: 135
<212> TYPE: DNA
<213> ORGANISM: artificial sequence
<220> FEATURE:
<223> OTHER INFORMATION: Epstein-Barr virus Zebra protein transduction
      domain MD11

<400> SEQUENCE: 12
aagcgataca agaatcgggt ggcttccaga aaatgccggg ccaagtttaa gcaactgctg      60
cagcactacc gtgaggtcgc tgctgccaaa tcatctgaaa tgacaggct gcgcctcctg     120 ttgaagcaga tgtgc                                                     135

<210> SEQ ID NO 13
<211> LENGTH: 45
<212> TYPE: PRT
<213> ORGANISM: artificial sequence
<220> FEATURE:
<223> OTHER INFORMATION: Epstein-Barr virus Zebra protein transduction
      domain MD11

<400> SEQUENCE: 13

Lys Arg Tyr Lys Asn Arg Val Ala Ser Arg Lys Cys Arg Ala Lys Phe
1               5                   10                  15

Lys Gln Leu Leu Gln His Tyr Arg Glu Val Ala Ala Ala Lys Ser Ser
            20                  25                  30

Glu Asn Asp Arg Leu Arg Leu Leu Leu Lys Gln Met Cys
        35                  40                  45

<210> SEQ ID NO 14
<211> LENGTH: 60
<212> TYPE: DNA
<213> ORGANISM: artificial sequence
<220> FEATURE:
<223> OTHER INFORMATION: primer

<400> SEQUENCE: 14
ggaattccat atgcatcatc atcatcatca tcatcacaag cgatacaaga atcgggtggc      60

<210> SEQ ID NO 15
<211> LENGTH: 35
<212> TYPE: DNA
<213> ORGANISM: artificial sequence
<220> FEATURE:
<223> OTHER INFORMATION: primer

<400> SEQUENCE: 15
ggaattccat atgccgaaac caatcaatgt ccgag                                 35

<210> SEQ ID NO 16
<211> LENGTH: 28
<212> TYPE: DNA
<213> ORGANISM: artificial sequence -continued
<220> FEATURE:
<223> OTHER INFORMATION: primer

<400> SEQUENCE: 16
cccaagcttg cacatctgct tcaacagg                    28

<210> SEQ ID NO 17
<211> LENGTH: 31
<212> TYPE: DNA
<213> ORGANISM: artificial sequence
<220> FEATURE:
<223> OTHER INFORMATION: primer

<400> SEQUENCE: 17
cccaagctta tgccgaaacc aatcaatgtc c                 31

<210> SEQ ID NO 18
<211> LENGTH: 33
<212> TYPE: DNA
<213> ORGANISM: artificial sequence
<220> FEATURE:
<223> OTHER INFORMATION: primer

<400> SEQUENCE: 18
ccgctcgagt tacttgtaca gctcgtccat gcc               33

<210> SEQ ID NO 19
<211> LENGTH: 30
<212> TYPE: DNA
<213> ORGANISM: artificial sequence
<220> FEATURE:
<223> OTHER INFORMATION: primer

<400> SEQUENCE: 19
ccgctcgagt taccgctcca gctgcttctg                   30

<210> SEQ ID NO 20
<211> LENGTH: 27
<212> TYPE: DNA
<213> ORGANISM: artificial sequence
<220> FEATURE:
<223> OTHER INFORMATION: primer

<400> SEQUENCE: 20
cccaagcttc cgctccagct gcttctg                      27

<210> SEQ ID NO 21
<211> LENGTH: 32
<212> TYPE: DNA
<213> ORGANISM: artificial sequence
<220> FEATURE:
<223> OTHER INFORMATION: primer

<400> SEQUENCE: 21
cccaagctta agcgatacaa gaatcgggtg gc                32

<210> SEQ ID NO 22
<211> LENGTH: 28
<212> TYPE: DNA
<213> ORGANISM: artificial sequence
<220> FEATURE:
<223> OTHER INFORMATION: primer

<400> SEQUENCE: 22
ccgctcgagg cacatctgct tcaacagg                     28

POLYPEPTIDES AND NUCLEIC ACIDS FOR TREATING ERBB2-DEPENDENT CANCERS

Figure 1:
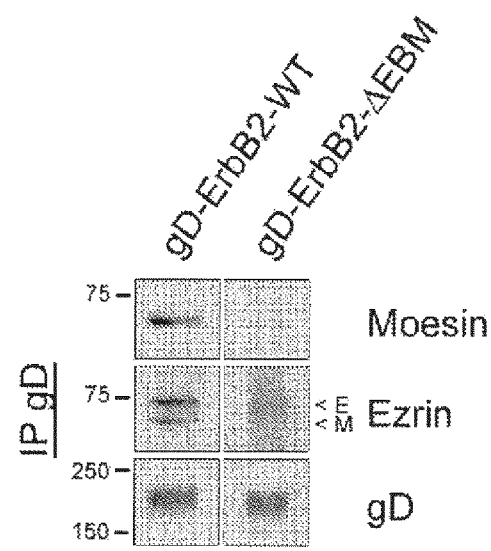

The present application (U.S. application Ser. No. 13/497,924) is a national stage filing based on PCT/EP2010/064055.

The present invention relates to polypeptides, nucleic acids and pharmaceutical compositions suitable for use in the treatment of ErbB2 dependent-cancers, in particular of tumors overexpressing ErbB2 or expressing mutated forms of the ErbB2 gene.

The tyrosine kinase receptor ErbB2 belongs to the ErbB family of receptors, which comprises four closely related members: EGF receptor (EGFR), ErbB2/Neu/HER2, ErbB3 and ErbB4 (Yarden et al. (2001) *Nat Rev Mol Cell Biol* 2:127-37). ErbB receptors are expressed in a variety of tissues of epithelial, mesenchymal and neuronal origin, where they play fundamental roles in development, proliferation, differentiation and angiogenesis (Russell et al. (1999) *Am J Physiol* 277:H2205-11). These receptors are activated by numerous ErbB-specific ligands that bind the extracellular domains and lead to the formation of both homo- and heterodimers (Olayioye et al. (2000) *Embo J.* 19:3159-67). However, ErbB2 has no known specific ligand, but it is the preferred heterodimerisation partner of the other ligand-bound family members to amplify mitogenic signalling. These distinctive properties of ErbB2 are explained structurally by an open configuration of its extracellular domain, which mimics the activated ligand-bound state of EGFR. Intriguingly, this structure does not lead readily to ErbB2 activation. Ligand-independent activation which is unique to the ErbB2 receptor occurs only with high surface overexpression (Di Fiore et al. (1987) *Science* 237:178-82), in the context of a transmembrane domain Val 664 to Glu point mutation neu in rat ErbB2 (Bargmann et al. (1986) *Cell* 45:649-57) or in the context of mutation in the ErbB2 kinase domain (Lee et al. (2006) *Clin Cancer Res* 12:57-61). Deregulated expression of ErbB2, which induces its homodimerisation and ligand-independent activation has been implicated in the development and malignancy of numerous types of human cancers (Yarden et al. (2001) *Nat Rev Mol Cell Biol* 2:127-37).

Currently, anti-ErbB2 antibodies (like Herceptin® or Transtuzumab (Bublil et al. (2007) *Proteins* 68:294-304)) are used to prevent accumulation of ErbB2 at the cell surface and thus activation of its homodimers. Such antibodies are used in combination with chemotherapy in the treatment of some breast cancers in which cancer cells over-express ErbB2. However, only 27% of patients respond to this treatment which is, in any case, not efficient against ErbB2 ligand-independent activation due to mutated forms of ErbB2 without extracellular domain.

Furthermore, clinic trials are now carried out on small molecules (like lapatanib or catertinib (Spector et al. (2007) *Breast Cancer Res* 9:205)) which are able to inhibit the kinase activity of ErbB2. However, these compounds present little specificity against the kinase activity of ErbB2 and inhibit also the kinase activity of other kinases. This lack of specificity leads to undesirable toxic effects (Spector et al. (2007) *Breast Cancer Res* 9:205).

There is thus a need for developing new methods for treating cancers which involves an over-activation of ErbB2.

ERM (Ezrin, Radixin, Moesin) family members are involved in many cellular processes, including regulation of actin cytoskeleton, control of cell shape, adhesion and motility and modulation of signalling pathways. ERM proteins are localised at cell-surface structures such as microvilli, ruffling membranes and cell-adhesion sites (Bretscher et al. *Nat Rev Mol Cell Biol* 19:51-6). They provide a regulated structural link between membrane proteins and the cortical cytoskeleton by interacting with cytoplasmic portions of adhesion molecules and phosphatidylinositol 4,5-bisphosphate ($PI_{4,5}P_2$) through their amino-terminal FERM domain, and with F-actin through their C-terminal domain. In the cytosol, ERM proteins exist in a closed form in which the FERM domain binds the C-terminal tail domain, preventing interaction with their functional binding partners. The activation of ERM proteins occurs through conformational changes triggered by binding to $PI_{4,5}P_2$ through the FERM domain and the phosphorylation of a conserved threonine in the C-terminal actin binding site (T567 in ezrin). Activated ERM proteins bind to a positively charged amino acid cluster containing a RxxTYxVxxA sequence motif present in the juxtamembrane domain of several adhesion molecules, including the hyaluronate receptor CD44, the sialomucin CD43, and the immunoglobulin-superfamily membrane proteins, ICAM-1, -2 and -3. Interaction of adhesion molecules with ERM proteins controls their cellular localisation within epithelial microvilli or lymphocyte uropods. ERM proteins also control the membrane recycling of several G protein-coupled receptors and tyrosine kinase receptors, including EGFR, through interaction with the PDZ domain-containing adaptors NHERF1 and 2. It was also shown that ezrin is involved in a specific pathway mediating cell survival of epithelial cells (WO 99/47150). Phosphorylation of the Tyr353 in the C-terminal domain of the ezrin protein impairs the ability of epithelial cells to survive in collagen matrix in inducing apoptosis, and those phosphorylated ezrin may thus be used in the treatment of tumors.

ERM-like proteins containing a FERM domain, like the merlin protein, were also identified. Merlin, was shown to be implicated in neurofibromatosis. Indeed, the lack of merlin was reported to result in an increase of the phosphorylation of ErbB2 which, in turn, induces an activation cascade implicating Src proteins and leading to an increase in cellular growth (Houshmandi et al. (2009) *Molecular and Cell Biology* 29 (6): 1472-1486). It was also shown that, in cells, the merlin protein is capable of binding to ErbB2 and, in vitro, that this binding occurs through its C-terminal domain which does not contain the FERM domain. The absence of merlin in glial cells results in a significant decrease in the formation of ErbB2-comprising heterodimeric receptors.

It was previously shown that adhesion of the human pathogen *Neisseria meningitidis* (also known as meningococcus) to human endothelial cells promotes the ligand-independent activation of ErbB2 (Hoffmann et al. (2001) *J Cell Biol* 155:133-143). Adhesion of *N. meningitidis* to human endothelial cells induces the specific clustering and tyrosine phosphorylation of ErbB2, and not of the other ErbB family members, at sites of bacterial adhesion. ErbB2 is clustered within structures resembling epithelial microvilli that surround bacteria and provokes their internalisation within intracellular vacuoles (Eugene et al. (2002) *J Cell Sci* 115:1231-41). Ezrin and moesin are key molecules in the organisation of the molecular complexes leading to the formation of these membrane protrusions by supporting the clustering of the ERM-binding adhesion molecules CD44, ICAM-1, ICAM-2 and the localised polymerisation of cortical actin.

The present invention arises from the unexpected finding that the ERM proteins are able to interact with ErbB2 via their FERM domain and that this interaction prevents the ligand-independent activation of ErbB2 and consequently downstream signalling events leading to cell proliferation. Surprisingly, it was shown that this interaction has no effect on the ErbB2 ligand-dependent activation which occurs when ErbB2 is in heterodimers with another family member. The inventors have also shown that the expression of ERM proteins in ErbB2-dependent breast cancer cells can efficiently inhibits ErbB2 activation and downstream signalling cascades

SUMMARY OF THE INVENTION

The present invention thus relates to at least one polypeptide
(i) comprising or consisting of the sequence of the FERM domain of an ERM protein, or
(ii) comprising or consisting of a sequence derived from the sequence of the FERM domain of an ERM protein by substitution, deletion, or insertion of at least one amino acid, provided that said polypeptide comprising or consisting of the sequence derived from the sequence of the FERM domain of an ERM protein is liable to prevent the ligand-independent activation of ErbB2 in cells, for use as a medicament.

The present invention also relates to a fusion polypeptide comprising or consisting of
(i) the FERM domain of an ERM protein, or
(ii) a polypeptide of sequence derived from the FERM domain of an ERM protein by substitution, deletion, or insertion of at least one amino acid, provided that said polypeptide comprising or consisting of the sequence derived from the FERM domain of an ERM protein is liable to prevent the ligand-independent activation of ErbB2 in cells,
linked to a polypeptide comprising a protein transduction domain, a cell penetrating peptide or a cell targeting peptide.

The present invention also relates to at least one nucleic acid encoding at least one polypeptide
(i) comprising or consisting of the sequence of the FERM domain of an ERM protein, or
(ii) comprising or consisting of a sequence derived from the sequence of the FERM domain of an ERM protein by substitution, deletion, or insertion of at least one amino acid, provided that said polypeptide comprising or consisting of the sequence derived from the sequence of the FERM domain of an ERM protein is liable to prevent the ligand-independent activation of ErbB2 in cells, for use as a medicament.

The present invention in particular relates to a nucleic acid encoding a fusion polypeptide comprising or consisting of
(i) the FERM domain of an ERM protein, or
(ii) a polypeptide of sequence derived from the FERM domain of an ERM protein by substitution, deletion, or insertion of at least one amino acid, provided that said polypeptide comprising or consisting of the sequence derived from the FERM domain of an ERM protein is liable to prevent the ligand-independent activation of ErbB2 in cells,
linked to a polypeptide comprising a protein transduction domain, a cell penetrating peptide or a cell targeting peptide.

The present invention also relates to a recombinant vector comprising a nucleic acid as described above.

The present invention also relates to an isolated host cell comprising the recombinant vector as described above.

A method of producing a polypeptide which comprises
(i) cloning a nucleic acid as described above into an expression vector,
(ii) transforming a host cell with the vector,
(ii) culturing the host cell under conditions suitable for the nucleic acid expression, makes also part of the invention.

DETAILED DESCRIPTION OF THE INVENTION

Polypeptides

As used herein, the term "polypeptide" includes any peptide or protein comprising two or more amino acids joined to each other by peptide bonds or modified peptide bonds. This term refers both to short chains (peptides and oligopeptides) and to longer chains (proteins) and further to peptidomimetics, such as peptoids and semipeptoids which are peptide analogs, which may have, for example, modifications rendering the peptides more stable while in a body, or more immunogenic. Such modifications include, but are not limited to, cyclization, N-terminus modification, C-terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modification and residue modification. Methods for preparing peptidomimetic compounds are well known in the art and are specified in Quantitative Drug Design, C A. Ramsden Gd., Chapter 17.2, F. Choplin Pergamon Press (1992).

As used herein, the term "amino acid" is understood to include: the 20 naturally occurring amino acids i.e. alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine; amino acids harbouring the post-translational modifications which can be found in vivo such as hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

A polypeptide may preferably consist of more than 50 amino acids, also preferably more than 150 amino acids, more preferably more than 250 amino acids, still preferably more than 290 amino acids. Also, a polypeptide may consist of less than 600, 550, 500, 400 amino acids.

Preferably, the polypeptide comprises or consists of the sequence of the FERM domain of an ERM protein. ERM family proteins are known to crosslink actin filaments with plasma membranes. As intended herein the "ERM family" comprises ezrin, radixin, moesin and the merlin ERM-like protein. Preferably, the FERM domain of an ERM protein according to the invention is selected from the group consisting of the ezrin FERM domain (represented by SEQ ID NO: 1), the moesin FERM domain (represented by SEQ ID NO: 2), the radixin FERM domain (represented by SEQ ID NO: 3) and the merlin FERM domain (represented by SEQ ID NO: 4).

More preferably, the polypeptide consists of the sequence of the FERM domain of an ERM protein selected from the group consisting of SEQ ID NO: 1, SEQ ID NO: 2, SEQ ID NO: 3 and SEQ ID NO: 4.

The polypeptide can also preferably comprise or consist of a fragment of the sequence of the FERM domain of an ERM protein. As used herein, the term "fragment" refers to a polypeptide shorter than the FERM domain and which amino acid chain consists of consecutive amino acids of the FERM domain. The fragments may comprise for example at least 20, 50, 100, 200 or 250 consecutive amino acids of a FERM domain.

Preferably, when the fragment is a fragment of SEQ ID NO: 1, SEQ ID NO: 2, SEQ ID NO: 3 or SEQ ID NO: 4 it exhibits at least 80%, more preferably at least 90%, and most preferably at least 95% identity with the sequence of SEQ ID NO: 1, SEQ ID NO: 2, SEQ ID NO: 3 or SEQ ID NO: 4, respectively.

Also preferably, the polypeptide according to the invention comprises or consists of a sequence derived from the sequence of the FERM domain of an ERM protein domain by substitution, deletion, or insertion of at least one amino acid, or of a sequence derived from a fragment of the sequence of the FERM domain of an ERM protein by substitution, deletion, or insertion of at least one amino acid.

Preferably, when the sequence is a sequence derived from SEQ ID NO: 1, SEQ ID NO: 2, SEQ ID NO: 3 or SEQ ID NO: 4, or derived from a fragment of SEQ ID NO: 1, SEQ ID NO: 2, SEQ ID NO: 3 or SEQ ID NO: 4, it exhibits at least 80%, more preferably at least 90%, and most preferably at least 95% identity with the sequence of SEQ ID NO: 1, SEQ ID NO: 2, SEQ ID NO: 3 or SEQ ID NO: 4 respectively.

As intended herein, the percentage of identity between two sequences is obtained by aligning the two sequences so as to maximize the number of positions of each sequence for which the amino acid are identical and dividing the number of positions of each sequence for which the amino acids are identical by the number of amino acids of the longer of the two sequences.

According to the invention, the polypeptide can consist of the sequence of the wild-type ERM protein: ezrin, moesin, radixin and merlin (represented by SEQ ID NO: 5, SEQ ID NO: 6, SEQ ID NO: 7 and SEQ ID NO: 8 respectively).

Preferably, the polypeptide is able to directly interact with ErbB2. For example, the polypeptide according to the invention can consists in an ERM protein mutant which is in an active opened form which enables it to interact with ErbB2. As intended herein "active opened form" refers preferably to an ERM protein form in which the C-terminal tail does not interact with the FERM domain.

Examples of ERM mutant which are constitutively in an active opened form, include an ERM mutant mimicking a phosphorylated form of the ERM protein, such as an ezrin mutant having a T567D mutation, an ezrin mutant deleted from the two residues at its C-terminal end, i.e. amino acids 1 to 584 of SEQ ID NO:5, (Gary et al. (1995) *Molecular Biology of the Cell* 6: 1061-75) or an ezrin mutant which consists in the first 575 amino acid of the wild-type ezrin (SEQ ID No:5) (Pearson et al. (2000) *Cell* 101 (3):259-70).

Preferably, the polypeptide is an ezrin mutant in which the tyrosine in position 353 is not mutated. Also preferably, the polypeptide is an ezrin mutant in which the 149-168 domain is not mutated.

The polypeptide may be a fusion polypeptide.

"Fusion protein" or "fusion polypeptide" refers to a polypeptide having at least two portions fused in frame and covalently linked together by a peptide bond, where each of the portions is a polypeptide having a different property.

For example, it is often advantageous to include one or more additional amino acid sequences which may contain secretory or leader sequences, pro-sequences, sequences which aid in purification, for example an histidine tag, or sequences that confer higher protein stability, for example during recombinant production.

Alternatively or additionally, the polypeptide may be fused with another polypeptide which comprises or consists of a sequence which allows transduction in the cell cytoplasm preferably without toxicity, like a protein transduction domain (PDT), a cell penetrating peptide, or a cell targeting peptide (in particular a breast, ovarian, bladder, colorectal or gastric cancer cell targeting peptide). Examples of protein transduction domains or cell penetrating peptides are the Epstein-Barr virus Zebra protein transduction domain MD11 (The DNA and protein sequences of which are notably represented by SEQ ID NO: 12 and SEQ ID NO: 13) (described in Rothe et al (2008) *Curr Protoc Protein Sci* 18: 18.11), the HIV TAT transduction domain (notably described in Snyder et al. (2005) *Cancer Res* 65 (23): 10646-50, Asoh et al. (2008) *Adv Drug Deliv Rev* 60 (4-5): 499-516), the Antennapedia homeodomain (Antp) protein from *Drosophila* and in particular the penetratin peptide (Derossi et al (1996) *J. Biol. Chem.* 271: 18188-18193, Derossi et al (1998) *Trends Cell Biol* 8: 84-87), the VP22 protein from herpes simplex virus, transportan (Pooga et al. (2001) *FASEB J.* 15: 1451-1453), FGF-4, MPG (Rothe et al. (2008) *Curr Protoc Protein Sci* 18: 18.11), a polyarginine peptide (Matsui et al. (2003) *Nippon Yakurigaku Zasshi.* 121: 435-439) (Michiue et al. (2005) *J Biol Chem* 280 (9):8285-9) and a polyhistidine peptide (Ranki et al. (2007) *Gene Ther.* 14 (1): 58-67), and a polyarginine peptide.

Examples of suitable cell targeting peptides are a peptide derived from the V1 peptide of the viral chemokine vMIP-II which antagonizes CXCR4 function (Zhou et al. (2002) *J Biol Chem* 277: 17476-85) in particular the V1 peptide of SEQ ID NO: 9 or its derivative the DV3 peptide of SEQ ID NO: 10 containing L-isomer residues, as breast cancer cells may express the CXCR4 receptor.

More preferably, the protein transduction domain (PDT), the cell penetrating peptide or the cell targeting peptide is the Epstein-Barr virus Zebra protein transduction domain, the HIV TAT protein transduction domain, penetratin, a V1 or DV3 peptide derived from the viral chemokine vMIP-II and a polyarginine peptide Also alternatively or additionally, the polypeptide may be fused with another polypeptide, preferably in a globular conformation, which can, after interaction with ErbB2, exert a molecular constraint on its juxtamembrane domain, in particular due to an allosteric effect, and which results in the disruption or ErbB2 self association. An example of such polypeptides can be GFP or albumin.

The polypeptide can also be fused with a polypeptide which such as an antibody or a peptide (specific targeting peptide) which can specifically recognizes tumour cells in order to specifically target the tumor cells.

The fusion of the two polypeptides can be realized at the carboxy-terminal or the amino-terminal end of each of them.

As intended herein the "amino-terminal end" of a polypeptide refers to the start of polypeptide terminated by an amino acid with a free amine group (—NH2). The carboxy-terminal end of a polypeptide refers to the end of the amino acid chain terminated by a free carboxyl group (—COOH).

In the fusion polypeptides, a polypeptide comprising or consisting in the sequence of the FERM domain of an ERM protein, a polypeptide comprising or consisting of a fragment of the sequence of the FERM domain of an ERM protein or a polypeptide comprising or consisting of a sequence derived from the sequence of the FERM domain of an ERM protein is more preferably linked at is carboxy-terminal end to the other polypeptide.

For example, the fusion polypeptide comprises a polypeptide comprising or consisting in the sequence of the FERM domain of an ERM protein, a polypeptide comprising or consisting of a fragment of the sequence of the FERM domain of an ERM protein or a polypeptide comprising or consisting of a sequence derived from the sequence of the FERM domain of an ERM protein linked, preferably at it carboxy-terminal end, to a polypeptide.

Preferably, the fusion polypeptide comprises a polypeptide consisting of the sequence of the FERM domain of an ERM protein linked, preferably at it carboxy-terminal end, to a polypeptide comprising or consisting of a protein transduction domain, a cell penetrating peptide or a cell targeting peptide, more preferably selected from the group consisting of the Epstein-Barr virus Zebra protein transduction domain, the HIV TAT transduction domain, penetratin, a V1 or DV3 peptide derived from the viral chemokine vMIP-II and a polyarginine peptide. More preferably the polypeptide consists in SEQ ID NO: 1, SEQ ID NO: 2, SEQ ID NO: 3 or SEQ ID NO: 4, even more preferably SEQ ID NO: 1, linked at its carboxy-terminal end to a Zebra protein or to its transduction domain.

Preferably, the polypeptide is liable to prevent the ligand-independent activation of ErbB2 in cells.

ErbB2 is a tyrosine kinase receptor of the EGF family of receptors.

By "ligand independent activation of ErbB2" is intended herein an ErbB2 activation which is not due to the ligand dependent activation of ErbB2 in heterodimers, with another receptor of the EGF receptor family.

For example, ligand-independent activation can be due to ErbB2 homodimerisation resulting from its over-expression in the cells, or from ErbB2 mutations inducing its activation or facilitating its homodimerisation.

The expression <<liable to prevent ligand-independent activation>> as intended herein refers to the ability to prevent the ErbB2 activation which is independent from ligand. Preferentially, this ability is that of a polypeptide according to the invention. This ability can consist in the prevention of ErbB2 phosphorylation which is responsible for activation. For example, it may block ErbB2 in a catalytic repressed state, in particular, in restricting access of the kinase domain to substrate tyrosine. Also preferably, preventing ligand-independent ErbB2 activation may result from the ability of a polypeptide to inhibit the formation of ErbB2 homodimers.

The polypeptide which is liable to prevent ligand-independent activation has preferably no effect on the ligand-dependent activation of ErbB2 in heterodimers with other family members such as EGFR or ErbB3.

Nucleic Acids and Production of Polypeptides

As intended herein the expression "nucleic acid" refers to any type of nucleic acid, it can notably be natural or synthetic, DNA or RNA, single or double stranded. In particular, where the nucleic acid is synthetic, it can comprise non-natural modifications of the bases or bonds, in particular for increasing the resistance to degradation of the nucleic acid. Where the nucleic acid is RNA, the modifications notably encompass capping its ends or modifying the 2' position of the ribose backbone so as to decrease the reactivity of the hydroxyl moiety, for instance by suppressing the hydroxyl moiety (to yield a 2'-deoxyribose or a 2'-deoxyribose-2'-fluororibose), or substituting the hydroxyl moiety with an alkyl group, such as a methyl group (to yield a 2'-O-methyl-ribose).

The terms "vector", "cloning vector" and "expression vector" as used herein denote the vehicle by which a DNA or RNA sequence can be introduced into a host cell so as to transform the host cell and to promote the expression of the introduced sequence. This introduction can, for example, be performed in order to allow the production of polypeptide encoded by the DNA or RNA sequence or for the purpose of gene therapy.

Examples of vectors include plasmids, phages and viruses. The most common vectors are plasmids which are autonomous replication units, generally of bacterial origin, and which may be double-stranded DNA. Plasmids can easily integrate an exogenous DNA sequence which can then easily be introduced into an appropriate host. A plasmid vector generally contains a coding DNA sequence, a promoter DNA sequence and has one or more restriction sites allowing an exogenous DNA to be introduced. Non-limiting examples of plasmids include the pKK (Clontech), pUC and pET (Novagen, Inc., Madison, Wis.), pRSET or pREP (Invitrogen, San Diego, Calif.), pMAL (New England Biolabs, Beverly, Mass.), or pGEX-4T-3 (Pharmacia) plasmids.

Preferably, the recombinant vector is an expression vector comprising a nucleic acid encoding a polypeptide according to the invention.

This expression vector can typically include the components of a cloning vector, such as, for example, an element that permits autonomous replication of the vector in the selected host organism and one or more phenotypically detectable markers for selection purposes. This expression vector normally comprises control nucleotide sequences encoding a promoter, operator, ribosome binding site, translation initiation signal and optionally, a repressor gene or one or more activator genes. The nucleic acid sequence according to the invention can also be cloned into expression vectors in order to create fusion with a tag. Example of such vectors are pRSET vectors (Invitrogen Corp., San Diego, Calif.), pQE30 (Qiagen) and preferably pCMV-HA (Clontech) and pCMV-myc (Clontech). The nucleic acid according to the invention can also be introduced into cells by viral delivery, in particular in the purpose of gene therapy. Preferably the vector is an adenoviral, retroviral, adeno-associated viral, lentiviral or a sendaiviral vector. Recombinant viruses are commonly used for gene transfer.

To date, the three most commonly used viruses for gene transfer are adenovirus, retrovirus and adeno-associated virus. More recently lentiviruses, a subgroup of the retroviruses, and sendaivirus are being used. Adenoviruses are able to transduce both dividing and non-dividing cells and can be produced at high viral titres. Retroviruses can infect dividing cells only and integrate their genome into the host chromosome.

Integration achieves long-term gene expression. Lentiviruses, a sub-family of retroviruses, share all the standard properties of retroviruses but in addition they have the capacity to transduce non-dividing cells. Adeno-associated virus (AAV) is a small, non-pathogenic, single-stranded DNA virus. It requires co-infection with a helper virus (adenovirus or herpes virus) in order to undergo productive infection. In the absence of helper virus, wild-type AAV integrates site-specifically, into the host genome. Similarly to retrovirus, integration facilitates longer gene expression. AAV can infect both non-dividing and dividing cells. Sendai virus is a member of the paramyxoviridae, and is a single-stranded RNA virus that is able to transfect both dividing and non-dividing cells. Its method of entering cells involves sialic acid and cholesterol that are common to many cell types. Sendai viral gene expression and replication are localized in the cytoplasm, in contrast to most viruses that need to enter the nucleus.

The expression "isolated host cell" according to the invention refers to any cell or organism which is selected, modified, cultivated or manipulated for the production of a substance by the cell, for example the expression by the cell of a gene, a DNA or RNA sequence, a protein or an enzyme.

Host cells include bacterial, archebacterial, fungal, plant, insect and animal cells, especially mammalian cells. Of particular interest are *E. coli, B. subtilis, S. aureus, S. cerevisiae, S. pombe, N. crassa*, SF9, C129, 293, NIH 3T3, CHO, COS, and HeLa cells.

Such cells can be transformed, transfected, or transduced by the recombinant vector according to the invention by any suitable method including electroporation, $CaCl_2$, $LiCl$, LiAc/PEG, spheroplasting, Ca-Phosphate, DEAE-dextran, liposome-mediated DNA uptake, injection, microinjection, microprojectile bombardment, or other established methods.

Polypeptides according to invention may be produced by any technique known in the art, such as, without limitation, any chemical, biological, genetic or enzymatic technique, either alone or in combination.

For example, the polypeptides according to the invention can be produced in a recombinant system. Preferably, the polypeptides carry additional sequence tags to facilitate purification. Such markers include tags. Non-limiting examples of tags include c-myc, haemagglutinin (HA), polyhistidine (6 times-His), GLU-GLU, and DYKDDDDK (FLAG®, SEQ ID NO: 11) tags. More preferably, the tag is a polyhistidine tag.

Host cells containing an expression vector according to the invention may be cultured under suitable conditions which allow expression of the polypeptide. Expression of the polypeptides may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Following expression, the protein tagged polypeptide can be extracted from a crude lysate of the host cell. The crude lysate of the host cells can be obtained by a variety of techniques known in the art, including enzymatic, chemical and/or osmotic lysis and physical disruption.

The polypeptide can then be purified by techniques well known from the person skilled in the art. For example, when a polyhistidine tag is used, the polypeptide can be purified on a Ni-column.

In some cases, it may be preferable to remove the tag (i.e., via protease cleavage) following purification.

Therapeutic Applications

The above polypeptides and nucleic acids can be used as medicament.

In particular, the medicament according to the invention is intended for treating a ErbB2-dependent cancer in patients.

As intended herein "ErbB2-dependent cancer" refers to cancer involving ErbB2 ligand-independent activation. Preferably, the ErbB2-dependent cancer according to the invention is selected from the group consisting of breast cancer, ovarian cancer, bladder cancer, colorectal cancer and gastric cancer.

According to the invention, the term "patient" or "individual" to be treated is intended for a human or non-human mammal (such as a rodent (mouse, rat), a feline, a canine, or a primate) affected or likely to be affected with cancer. Preferably, the subject is a human, man or woman.

The term "treating" or "treatment" means reversing, alleviating, inhibiting the progress of, or preventing the disorder or condition to which such term applies, or one or more symptoms of such disorder or condition. In particular, the treatment of the disorder may consist in destroying, depleting or inhibiting the proliferation of cancer cells. Most preferably, such treatment leads to the complete depletion of cancer cells.

The nucleic acid according to the invention can be used in gene therapy. "Gene therapy" as intended herein consists of the insertion of genes, preferably a gene coding for a polypeptide according to the invention, into an individual's cells and tissues to treat a disease, this integration resulting in the expression in the cells of the nucleic acid according to the invention.

The present invention also relates to pharmaceutical compositions. As intended herein, a "pharmaceutical composition" contains a polypeptide or nucleic acid according to the invention and pharmaceutically acceptable excipients and/or carriers, and optionally sustained-release matrices, such as biodegradable polymers.

Where combined therapy is contemplated, pharmaceutical compositions may also comprise with other molecules useful to treat cancer. Examples of such medicaments include cytotoxic agent such as gemcitabine, paclitaxel, cisplatin, etoposide and doxorubicin and mechanism-based agents such as (heat shock protein inhibitor) HSP90 inhibitors geldanamycin and its analogue 17-Allylamino-17-demethoxygeldanamycin (17-AAG or Tanespimycin) and the proteasome inhibitor bortezomib.

"Pharmaceutically" or "pharmaceutically acceptable" refers to molecular entities and compositions that do not produce an adverse, allergic or other untoward reaction when administered to a mammal, especially a human. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical or therapeutic compositions of the invention can be formulated for an intra-tumoral, topical, oral, parenteral, intranasal, intravenous, intramuscular, subcutaneous or intraocular administration and the like Preferably, the polypeptide according to the invention is targeted toward tumor cells. For that purpose, the pharmaceutical composition can be, preferably, administered by direct injection to tumor aggregates (intra-tumoral administration). The polypeptide according to the invention may also be delivered to tumor cells by liposomes carrying antibodies or peptides specific for tumor cells.

The patient according to the invention is preferably treated with a therapeutically effective amount of polypeptide of the invention. The term "therapeutically effective amount" is meant for a sufficient amount of polypeptide or nucleic acid in order to treat cancer, at a reasonable benefit/risk ratio applicable to any medical treatment.

It will be understood, however, that the total daily usage of the polypeptide and pharmaceutical compositions of the present invention will be decided by the attending physician within the scope of sound medical judgment. The specific therapeutically effective dose level for any particular patient will depend upon a variety of factors including the disorder being treated and the severity of the disorder; the activity of the polypeptide employed; the specific composition employed, the age, body weight, general health, sex and diet of the patient; the time of administration, route of administration, the duration of the treatment; the drugs used in combination or coincidental with the specific polypeptide employed; and like factors well known in the medical arts.

When gene therapy is contemplated and in order to improve the delivery of the new DNA into the cell, the nucleic acid or the recombinant vector according to the invention can be protected from damage and its entry into the cell can be facilitated. To this end molecules can be used as lipoplexes and polyplexes which have the ability to protect the DNA from undesirable degradation during the transfection process.

The invention will be further illustrated in view of the following figures and examples.

FIGURES

FIG. 1 depicts the interaction between ErbB2 (gD-ErbB2-WT) or ErbB2 without the ERM binding domain (gD-ErbB2-

ΔEBM) and ERM proteins Ezrin and Moesin in human endothelial cells (HBMECs) by co-immunoprecipitation with antibodies directed against the gD-tag (IP gD) and western blot performed with anti-moesin (Moesin), anti-ezrin (Ezrin) and anti-gD (gD) antibodies.

Figure 2:
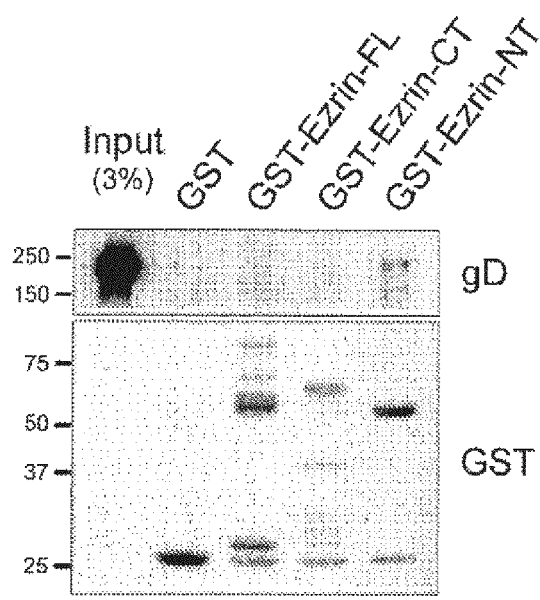

FIG. 2 depicts the interaction between GST alone or fused with full length ezrin (GST-Ezrin-FL), the amino-terminal domain (GST-Ezrin-NT) or the carboxy-terminal domain (GST-Ezrin-CT) of ezrin with ErbB2 (gD-ErbB2-WT) in a pull down assay and western blot with anti-gD (gD) or anti-GST (GST) antibodies.

Figure 3:
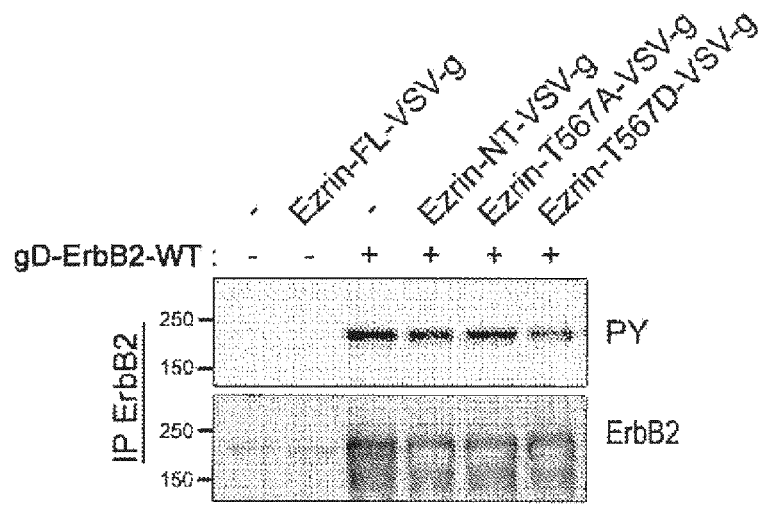

FIG. 3 depicts the effect of the phosphorylation state of ezrin on the tyrosine phosphorylation of overexpressed ErbB2. HBMECs cells were transfected with empty vector, vector encoding VSV-G-tagged forms of full length ezrin (Ezrin-FL-VSV-g), vector encoding ErbB2 (gD-ErbB2 WT) alone or together with VSV-g-tagged forms of the ezrin FERM domain (Ezrin-NT-VSV-g), VSV-g-tagged forms of the ezrin mutant mimicking the non-phosphorylated form (Ezrin-T567A-VSV-g) or VSV-g-tagged forms of the ezrin mutant mimicking the phosphorylated form (Ezrin-T567D-VSV-g), followed by co-immunoprecipitation with anti-ErbB2 antibodies (IP ErbB2) and western blot performed with anti-phosphotyrosine (PY) and anti-ErbB2 (ErbB2) antibodies on immunoprecipitated proteins.

Figure 4:
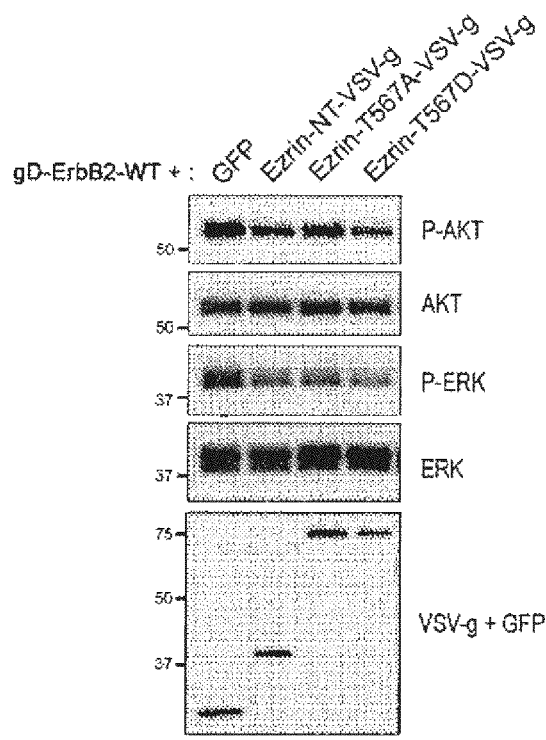

FIG. 4 depicts the effect of the tyrosine phosphorylation inhibition of ErbB2 promoted by the FERM domain of ezrin and the 1567D ezrin mutant on the activation of the mitogen-activated protein kinases (MAPK) Erk1/2 and AKT. HBMECs cells were transfected with vectors encoding ErbB2 (gD-ErbB2 WT) with GFP (GFP), VSV-g-tagged forms of the ezrin FERM domain (Ezrin-NT-VSV-g), VSV-g-tagged forms of the ezrin mutant mimicking the non-phosphorylated form (Ezrin-T567A-VSV-g) or VSV-g-tagged forms of the ezrin mutant mimicking the phosphorylated form (Ezrin-T567D-VSV-g) followed by western blot with anti-phospho-AKT (P-AKT), anti-AKT (AKT), anti-phospho-MAPK Erk1/2 (P-ERK), anti-ERK (ERK) and anti-VSV-g-tagged protein (VSV-g+GFP) antibodies.

Figure 5:
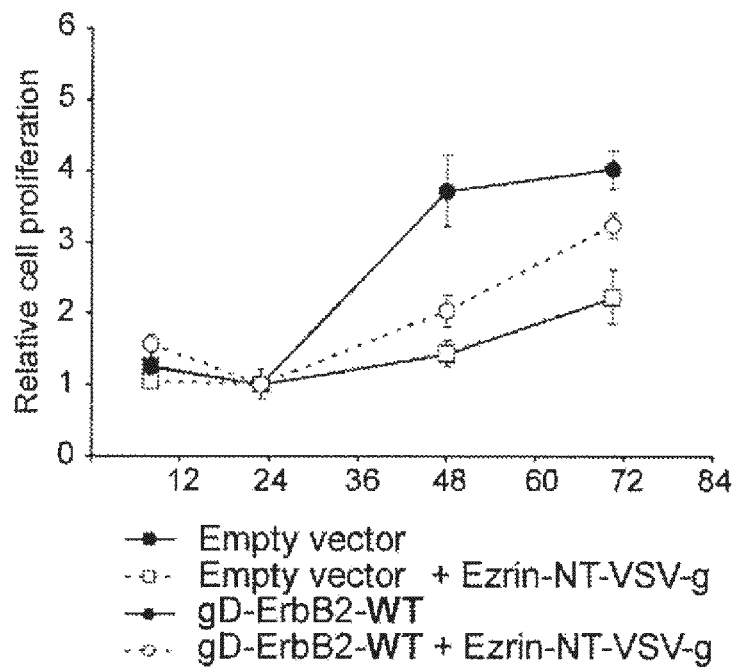

FIG. 5 depicts the effect of transfection of HBMECs cells with empty vector (Empty vector), empty vector and a vector encoding VSV-g-tagged forms of the ezrin FERM domain (Empty vector+Ezrin-NT-VSV-g), a vector encoding ErbB2 (gD-ErbB2-WT) alone or together with VSV-g-tagged ezrin FERM domain (gD-ErbB2-WT+Ezrin-NT-VSV-g) on HBMECs cells proliferation (Relative cell proliferation) in function of time after transfection (Hours).

Figure 6:
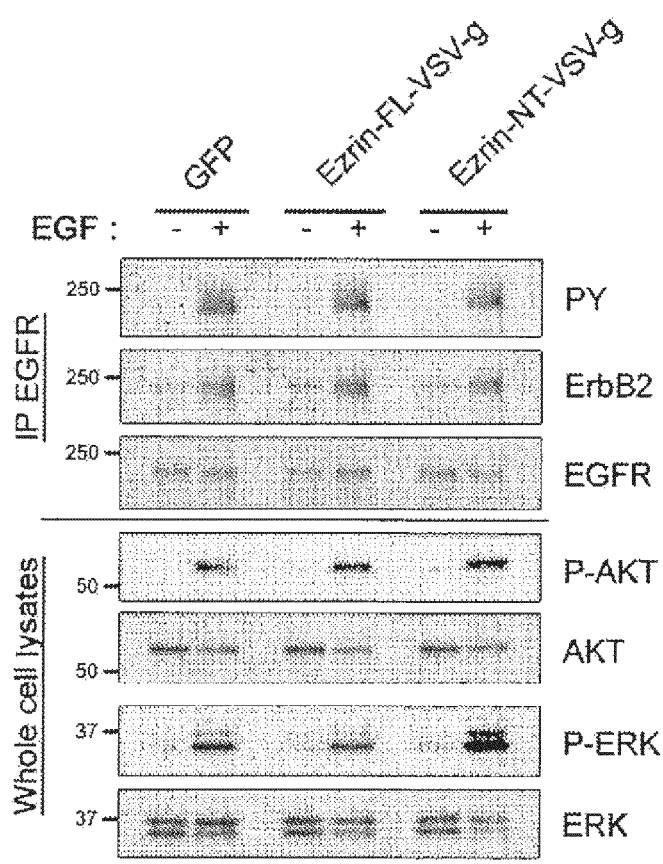

FIG. 6 depicts the effect of Ezrin on ligand dependent activation of ErbB2 by transfection of HBMECs with vectors encoding GFP, VSV g-tagged forms of the full length ezrin (Ezrin-FL-VSV-g) or VSV-g-tagged forms of the ezrin FERM domain (Ezrin-NT-VSV-g), untreated (−) or treated with 50 ng/ml EGF (+) for 5 min. After lysis, endogenous EGF receptors were immunoprecipitated (IP EGFR) and western blot was performed with anti-phosphotyrosine (PY), anti-ErbB2 (ErbB2) and anti-EGFR (EGFR) antibodies on immunoprecipitated proteins (upper panels). Western blot was also performed on whole cell lysates (Whole cell lysates) with anti-Phospho-AKT (P-AKT), anti-AKT (AKT), anti-phospho-ERK1/2 (P-ERK) and anti-ERK1/2 (ERK) antibodies (lower panels).

Figure 7:
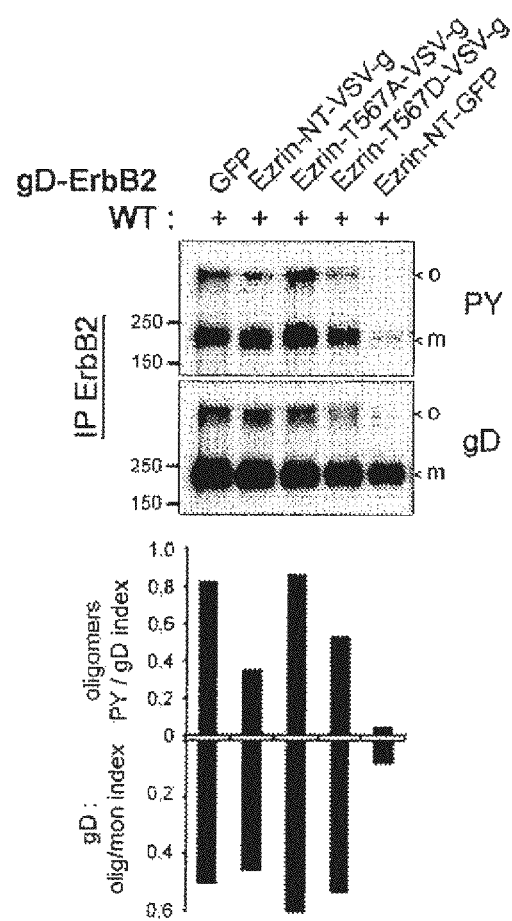

FIG. 7 depicts the altering effect of ezrin forms or of ezrin coupled to GFP on the ability of ErbB2 to self-associate. Transient transfection of HBMECs was carried out with vectors encoding ErbB2 (gD-ErbB2-WT) together with GFP (GFP) or with VSV-g-tagged forms of the ezrin FERM domain (Ezrin-NT-VSV-g), VSV-g-tagged forms of the ezrin mutant mimicking the non-phosphorylated form (Ezrin-T567A-VSV-g) or VSV-g-tagged forms of the ezrin mutant mimicking the phosphorylated form (Ezrin-T567D-VSV-g) or with GFP-tagged forms of the ezrin FERM domain (Ezrin-NT-GFP) followed by immunoprecipitation of ErbB2 monomers (m) or oligomers (o) with ErbB2 antibodies and western blot with anti-phosphotyrosine (PY) or anti-gD antibody (gD) antibodies (upper panel). The proportions of oligomeric (o), monomeric (m) and phosphorylated oligomeric ErbB2 were calculated using Image J. Histograms below the x axis represent the ratio of oligomers to monomers in the total ErbB2 pool and histograms above the x axis represent the ratio of phosphorylated oligomers to total oligomers (lower panel).

Figure 8:
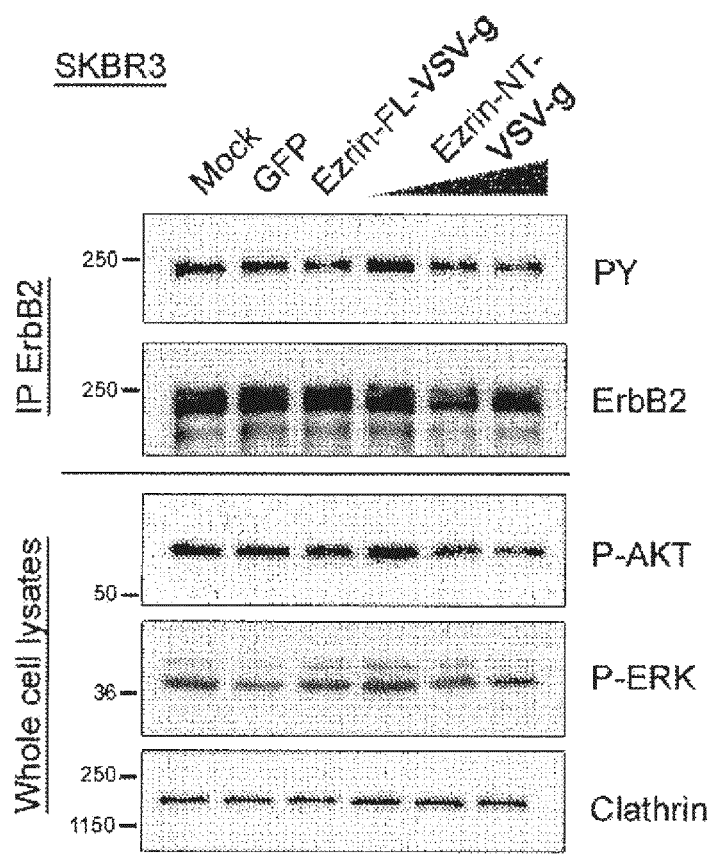

FIG. 8 depicts the effect exerted by ezrin on the constitutive activation of ErbB2 in the SKBR3 breast cancer cells after mock transfection or transfection with vector encoding GFP (GFP), VSV-g-tagged full length ezrin (Ezrin-FL-VSV-g) or increasing concentrations of VSV-g-tagged forms of the ezrin FERM domain (Ezrin-NT-VSV-g) followed by western blot with anti-phosphotyrosine (PY) or anti-ErbB2 antibodies after immunoprecipitation with anti-ErbB2 antibody (IP ErbB2) (upper panel) or followed by western blot on whole cell lysates with anti-phospho-AKT (P-AKT), anti-phospho-MAPK Erk1/2 (P-ERK) or anti-clathrin (Clathrin) antibodies.

Figure 9:
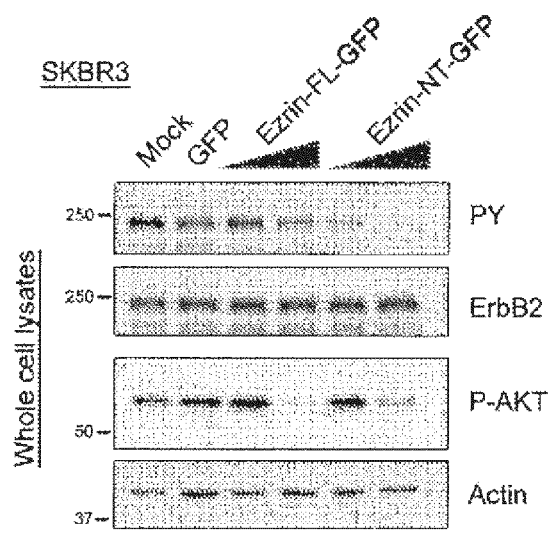

FIG. 9 depicts the effect exerted by ezrin coupled to GFP on the constitutive activation of ErbB2 in the SKBR3 breast cancer cells after mock transfection or transfection with vector encoding GFP (GFP), increasing concentration of VSV-g-tagged full length ezrin coupled with GFP (Ezrin-FL-GFP) or increasing concentrations of VSV-g-tagged forms of the ezrin FERM domain coupled with GFP (Ezrin-NT-GFP) followed by western blot on whole cell lysates with anti-phosphotyrosine (PY), anti-ErbB2, anti-phospho-AKT (P-AKT) or anti-actin (Actin) antibodies.

Figure 10:
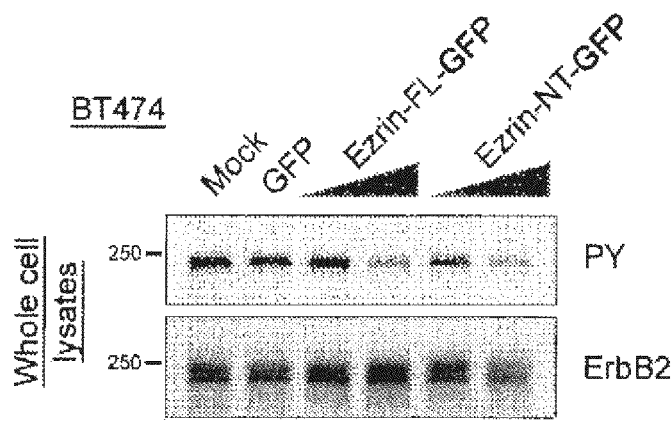

FIG. 10 depicts the effect exerted by ezrin coupled to GFP on the constitutive activation of ErbB2 in the BT474 breast cancer cells after mock transfection or transfection with vector encoding GFP (GFP), increasing concentration of VSV-g-tagged full length ezrin coupled with GFP (Ezrin-FL-GFP) or increasing concentrations of VSV-g-tagged forms of the ezrin FERM domain coupled with GFP (Ezrin-NT-GFP) followed by western blot on whole cell lysates with anti-phosphotyrosine (PY), anti-ErbB2 (ErbB2), anti-phospho-AKT (P-AKT) or anti-actin (Actin) antibodies.

Figure 11:
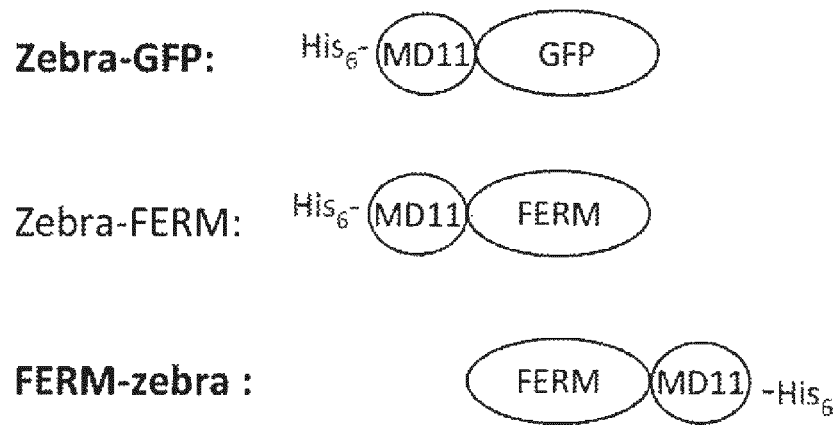

FIG. 11 depicts the various constructs comprising the ezrin FERM domain fused to the Zebra protein of Epstein-Barr virus, a 6 histidine-tag and possibly the GFP gene.

Figure 12:
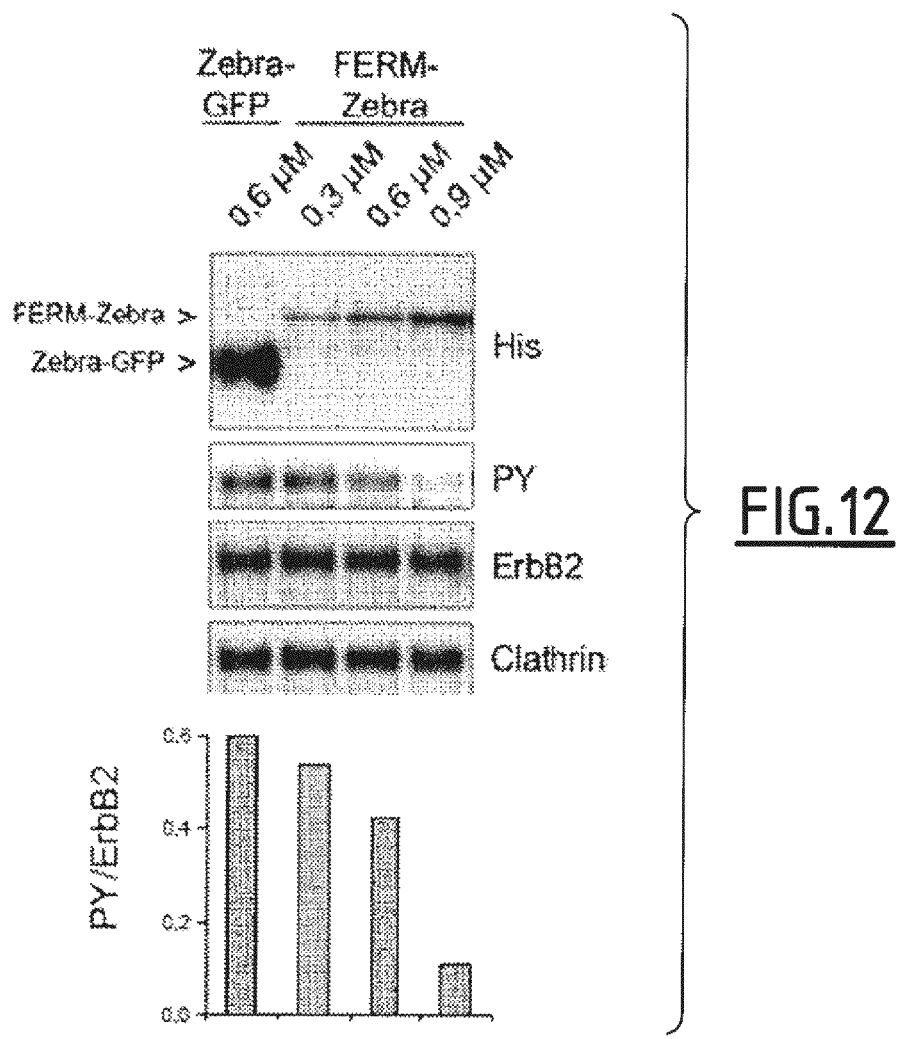

FIG. 12 depicts the effect exerted by transduction of Zebra in fusion with GFP at 0.3 µM (Zebra-GFP) or FERM in fusion with Zebra at 0.3 µM, 0.6 µM or 0.9 µM (FERM-Zebra) on the activation of ErbB2 in the SKBR3 breast cancer cells by western blot on whole cell lysates with anti-Histidine tag (His), anti-phosphotyrosine (PY), anti-ErbB2 (ErbB2) and anti-clathrin (Clathrin) antibodies (Upper panel). The histograms show the phosphorylated ErbB2/total ErbB2 ratio (PY/ErbB2) derived from the quantitative values obtained from the western blots (Lower panel).

Figure 13:
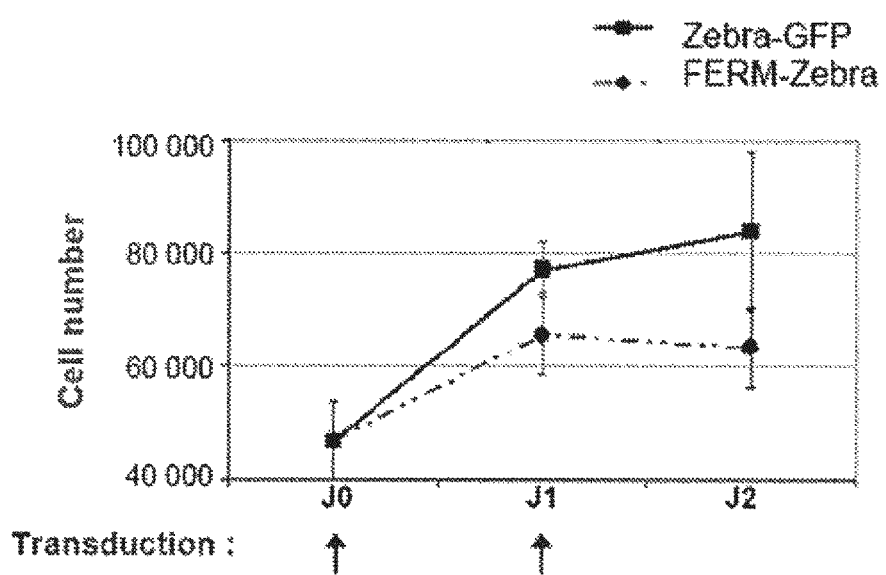

FIG. 13 depicts the effect exerted by transduction at day D0 and D1 of Zebra in fusion with GFP at 0.15 µM (Zebra-GFP) or FERM in fusion with Zebra at 0.9 µM in SKBR3 breast cancer cells at the day 0 (D0), day 1 (D1) or day 2 (D2) on the proliferation of these cells measured in number of cells.

EXAMPLES

Methods

Antibodies and Reagents.

Polyclonal antibodies directed against EGFR (1005) and ErbB2 (C-18) were purchased from Santa Cruz, Inc Biotechnology, mAb against ErbB2/HER2/Neu (Cl e2-4001+3B5) was from Thermo scientific. Antiphosphotyrosine antibody (PY20) was from Upstate, Anti-phospho Erk 1/2 (Thr202/Tyr204), anti-phospho AKT (Ser473), Anti-MAPK p44/p42 ERK1/2 and anti-AKT were from Cell Signaling Technology. Polyclonal antibody directed against ZO1 was from Zymed. Anti-GST and anti-VSV-g (clone P5D4) antibodies from Roche; Rhodamine-phalloidin from Sigma; Fluorescence-conjugated secondary antibodies, peroxidase-conjugated secondary antibodies and ECL reagents were from Jackson Immunoresearch Laboratories; Polyclonal antibodies against ezrin and moesin (Niggli et al (1995) FEBS Lett 376 (3): 172-6). Anti-glycoprotein-D (gD) antibody was obtained by Genentech, Inc (South San Francisco, Calif., USA), Bis(sulfosuccinimidyl)suberate ($BS^3$) from Pierce; EGF and Heregulin-1b were from BD bioscience.

Cell Culture, Bacterial Strain and Infection.

HBMECs (human bone marrow endothelial cells) (Schweitzer et al. (1997) Lab Invest 76:25-36) were cultured and infected with 2C43 (formerly clone 12), a piliated capsulated Opa⁻ variant of the serogroup C meningococcal strain 8013, as previously described (Hoffmann et al (2001) J Cell Biol 155:133-43, Lambotin et al. (2005) J Cell Sci 118:3805-16). The porcine kidney epithelial cell line LLC-PK1 and the human breast cancer cell lines SK-BR-3 and BT-474 were obtained from the American Type Culture Collection (Manassas, Va.) were maintained in DMEM containing 10% fetal bovine serum (FBS) under 5% $CO_2$ at 37° C.

Two-Hybrid Procedure.

To prepare the baits and the prey used in this paper, the cytosolic domains of ErbB2 (675-1255) or EGFR (669-1185) were fused to the LexA binding domain using the vector pBTM116, which encodes Trp.1 The amino-terminal domain of ezrin (1-223) or the PDZ domain of ERBIN (1240-1371) were fused to the GAL4 activation domain in pACT2 vector (Clontech) which encodes Leu2 as a selection marker. Interaction was demonstrated first by the capacity of co-transformed L40 yeast to grow on minimum medium that lacked tryptophan, leucine, and histidine, supplemented with 50 mM 3-aminotriazole (3-AT), b-galactosidase activity of colonies growing on these plates was then tested as previously described (Borg et al (2000) Nat Cell Biol 2:407-14, Jaulin-Bastard et al. (2001) J Biol Chem 276:15256-63).

cDNA Constructs and Cell Transfections.

Vectors encoding the gD-tagged Wild-type, V659E and VVI/AAA constructs of ErbB2 previously described (Penuel et al. (2002) J Biol Chem 277:28468-73) were obtained from Genentech, Inc (South San Francisco, Calif., USA). Three ErbB2 truncation mutants were generated by creating sequential C-terminal truncations at residues 676, 684 and 689, and an ErbB2 construct with mutations within the described ERM binding motif was generated by alanine and glycine substitutions. All mutations were generated with the QuikChange XL site-directed mutagenesis kit (Stratagene) using gD-ErbB2 construct in a pRK mammalian expression vector as a template. Vectors encoding the VSV-g tagged forms of ezrin, GFP-ezrin and GST-tagged ezrin plasmids were previously described (Gautreau et al. (2000) J Cell Biol 150:193-203) and vector encoding the GFP-FERM was kindly provided by Dr J. Delon (Institut Cochin, Paris, France). Vector encoding the chimeric molecule encompassing the extracellular domain of the EGFR fused to the transmembrane and intracellular domains of ErbB-2 (EGFR/ErbB2 chimera) (Segatto et al (1992) Oncogene 7 (7):1339-46). HBMECs and LLC-PK1 were transfected using the nucleofector system developed by Amaxa Inc or Biorad electroporation system, as previously described (Gautreau et al. (2000) J Cell Biol 150:193-203, Lambotin et al (2005) J Cell Sci 118:3805-16) respectively. SKBR3 and BT474 were transfected with Lipofectamin™ LTX Reagent supplemented with PLUS Reagent (Invitrogen) according to manufacturer's instructions.

Confocal Immunofluorescence Microscopy.

HBMECs were grown to confluence on Thermanox coverslips (LabTek). After infection, cells were fixed and labelled as previously described (Hoffmann et al. (2001) Cell Biol 155-133-143, Lambotin et al. (2005) J Cell Sci 118:3805-16). Transfected HBMECs and LLC-PK1 were plated on Thermanox coverslips at high density to reach confluency and HBMECs cells were either non infected or infected 24 h after transfection before fixation and staining, while LLC-PK1 were fixed 48 h after transfection. Series of optical sections were obtained with either a BIORAD MRC 1024 confocal microscope (Nikon Diaphot 300), using a 60× oil immersion objective, or a Leica TCS-SP5 resonant scanner multi-photon confocal microscope (Leica Microsystems), using a 63× oil immersion objective. Three-dimensional reconstructions and merged images of the same field were obtained using Imaris software (Bitplane Company).

Immunoprecipitations and Immunoblotting.

Cells were washed once with cold PBS and lysed in a Triton based-buffer (1% Triton, 50 mM Tris-HCl pH 8.8, 25 mM NaCl, 1 mM EDTA, 1 mM $NaVO_4$, 1 mM NaF, 1 mM AEBSF, 10 µg/ml each of aprotinin/leupeptin/pepstatin). The insoluble fraction was removed by centrifugation and the cleared lysates were used for immunoprecipitation with specific antibodies. Where indicated, cells were treated with 1 mM Bis(sulfosuccinimidyl)suberate ($BS^3$) for 40 min at 4° C., then incubated in 15 mM Tris pH 7.5 for 15 min at 4° C. according to manufacturer's instructions, prior to cell lysis. Precipitated proteins were separated on SDS-PAGE, transferred to nitrocellulose (Schleicher & Schuell). After blocking for 1 h in PBS/3% milk/0.1% Tween 20, filters were probed overnight with specific antibodies. Proteins were visualized with peroxidase-coupled secondary antibody using the ECL system (Amersham). Western blot quantifications were obtained with Image J software.

Pull Down Experiments.

HBMEcs non transfected or transfected with the plasmids indicated were lysed with RIPA buffer (50 mM Hepes pH 7.5, 150 mM NaCl, 1 mM EGTA, 1.5 mM $MgCl_2$, 10% glycerol, 0.1% SDS, 1% triton, 0.5% sodium deoxycholate, 1 mM $NaVO_4$, 1 mM NaF, 1 mM AEBSF, 10 µg/ml each of aprotinin/leupeptin/pepstatin). Clarified lysates were incubated with GST fusion proteins (20-30 mg) bound to glutathione-Sepharose beads for 2 h at 4° C. Beads were washed three times with lysis buffer, and bound proteins were eluted in Laemmli sample buffer and separated by SDS-PAGE for analysis by western blotting.

Proliferation Assays.

HBMECs transfected with the plasmids indicated were seeded at $60.10^3$ cells/well in 24 well plates and grown in complete medium for the times indicated. Cells were recovered using trypsin and counted. Duplicate counts for each of the four wells per condition were obtained.

Cloning of FERM-ZEBRA Protein.

The DNA fragments encoding the truncated form of ZEBRA was generated by PCR and ligated into the *Escherichia coli* expression vector pET15b (Novagen), which provided an N-terminal hexahistidine tag for subsequent purification.

Sequences of primers used for generation of truncated ZEBRA fragment, EGFP have been described previously (Rothe et al. (2008) *Curr Protoc Protein Sci* 18: 18.11) and listed below, together with the sequences of primers used for generation of FERM fragment fused to truncated ZEBRA fragment. The fusion proteins were cloned into the pET15b expression plasmid.

```
His-ZEBRAAS175Ndelfor (SEQ ID NO: 14):
5'-GGAATTCCATATGCATCATCATCATCATCATCATCACAAGCGA

TACAAGAATCGGGTGGC-3'

FERM-Ndel-for (SEQ ID NO: 15):
5'-GGAATTCCATATGCCGAAACCAATCAATGTCCGAG-3'

ZEBRAAS220-HindIII-rev (SEQ ID NO: 16):
5'-CCCAAGCTTGCACATCTGCTTCAACAGG-3'

FERM-HindIII-for (SEQ ID NO: 17):
5'-CCCAAGCTTATGCCGAAACCAATCAATGTCC-3'

GFP-XhoI-STOP-rev (SEQ ID NO: 18):
5'-CCGCTCGAGTTACTTGTACAGCTCGTCCATGCC-3'

FERM-XhoI-STOP-rev (SEQ ID NO: 19):
5'-CCGCTCGAGTTACCGCTCCAGCTGCTTCTG-3'

FERM-HindIII-rev (new) (SEQ ID NO: 20):
5'-CCCAAGCTTCCGCTCCAGCTGCTTCTG-3'

ZEBRA178-HindIII-for (SEQ ID NO: 21):
5-CCCAAGCTTAAGCGATACAAGAATCGGGTGGC-3'

ZEBRAAS220-XhoI-rev (SEQ ID NO: 22):
5'-CCGCTCGAGGCACATCTGCTTCAACAGG-3'
```

Expression and Purification of Recombinant Proteins.

Recombinant fusion proteins were expressed in *E. coli* BL21(DE3) after induction with 0.5 mM isopropyl_-D-thiogalactopyranoside for 15 h at 16° C. Cells were lysed by sonication in 20 mM Tris buffer (pH 6.8 or 8) containing 250 mM NaCl and 10% glycerol and subsequently treated with DNase I (Roche Applied Science) for nucleic acid removal. Purifications of His6-tagged proteins were performed by nickel affinity chromatography. Proteins were washed using a 0.5-1.5 M NaCl gradient and eluted in 500 mM imidazole, 20 mM Tris, 75 mM KCl, 0.5M NaCl, and 10% glycerol. All purification steps were carried out at 4° C. and in the presence of protease inhibitors (pepstatin, E-64, aprotinin, Pefabloc, and complete protease inhibitor mixture; Roche Applied Science). Prior to transduction experiments, purified proteins were dialyzed against phosphate-buffered saline (PBS).

Test of the Transduction Efficiency of Breast Tumor Cells Overexpressing ErbB2 with Zebra-GFP Fusion Protein.

The method used allows the production and purification of large quantities of proteins fused with Zebra with a degree of purity higher than 95% as described in Rothe et al. ((2008) *Curr Protic Protein Sci* 18:18. 11). Firstly, the efficiency of the technique was checked and optimal conditions were developed for the transduction of the Zebra-GFP protein in the tumor cells SKBR3 and BT474 which over-expressed ErbB2. The cells were put in the presence of various concentration of Zebra-GFP protein for two hours in a culture medium without serum, after two washes in PBS (this containing proteases likely degrade the fusion protein and to diminish the transduction efficiency). The cells were then washed and the transduction medium was replaced with fresh complete medium. Alternatively, the complete medium with serum was added to the cells without taking away the transduction medium. The vectorized protein penetration efficiency in the cells and its maintenance through time (4 h 30, 24 h and 48 h after the two hours of transduction) were measured by immunofluorescence and flow cytometry.

Measurement of Tumor Cell Proliferation after Transduction with the Fusion Proteins.

The cells were transduced with either Zebra-GFP or FERM-zebra proteins on day D for two hours in absence of serum (after two washes in PBS to take away any remaining serum). Then after adding complete medium with serum, they were grown for three days with or without further transductions on day 1 or day 2 under the same conditions as on day 0).

Results

Example 1

ErbB2 Interacts with the ERM Proteins Ezrin and Moesin

It was observed that unlike the other ErbB family members, ErbB2 possesses a RxxTYxVxxA sequence motif in its cytosolic juxtamembrane region, highly reminiscent of the ERM-binding sequence found in CD44, CD43, ICAM-1-3 (Hamada et of (2003) *Embo J* 22:502-14). Therefore, the ability of the ezrin FERM domain to interact with ErbB2 using a yeast two hybrid system was assessed. Cytosolic domains of ErbB2 or EGFR were used as bait in interactions with the amino-terminal domain of ezrin as prey, or with the PDZ domain of Erbin as a control. As expected, ERBIN PDZ domain, which directly binds to the C-terminal amino acids of ErbB2 but not with those of other related RTKs, interacted with the cytosolic domain of ErbB2 but not that of EGFR. In addition, an interaction was detected between the amino-terminal domain of Ezrin and the cytosolic domain of ErbB2, while no interaction was observed with the cytosolic domain of EGFR.

To address the interaction between ErbB2 and ERM proteins, a gD-tagged form of ErbB2 containing multiple substitutions in the ezrin binding motif was generated by targeted mutagenesis: in this mutated form (gD-ErbB2-ΔEBM for gD-ErbB2 ΔERM binding motif), the basic cluster KRR (676-678) and two supposed key residues R683 and Y685 were replaced with alanine or glycine residues. Both the wild-type and mutated forms of gD-tagged ErbB2 were expressed in human endothelial cells and could be detected in equivalent quantity at the cell plasma membrane. Their ability to interact with endogenous ERM proteins was assessed by co-immunoprecipitation experiments. Ezrin and moesin were both immuno-precipitated with wild-type ErbB2, and, as expected, these interactions were affected by mutations in the ezrin binding domain (FIG. 1).

To further characterise the interaction between ErbB2 and Ezrin, the gD-tagged forms of ErbB2 were expressed in human endothelial cells and receptors were precipitated in a pull-down assay with GST fusion proteins containing either full length ezrin (FL), the amino-terminal domain (NT or FERM domain) or the carboxy-terminal domain (CT) of ezrin (FIG. 2). It was found that ErbB2 interacts with the N-terminal domain of ezrin, but not with full-length ezrin, nor the C-terminus of ezrin. These data indicate that the N-terminal domain of ezrin is necessary and sufficient for its interaction with ErbB2. Moreover, they indicate that the ErbB2 binding site of ezrin is masked in full-length ezrin due to the intramolecular interaction between the N- and C-terminal domains of ezrin. As expected, targeted mutagenesis in the ezrin binding motif of ErbB2 considerably reduced ErbB2 binding to the ezrin FERM domain. In addition, endogenous ErbB2 was pulled down with the N-terminal domain of ezrin, while endogenous EGFR was found not to interact with ezrin in any form.

Altogether, these results indicate that ErbB2 selectively interacts with the membrane-cytoskeleton linkers ezrin and moesin. The juxtamembrane region of ErbB2 contains an effective ERM binding motif allowing its interaction with the ezrin FERM domain.

Example 2

ERM Proteins Control ErbB2 Localisation within Microvilli Type Structures

Since adhesion of *N. meningitidis* to human endothelial cells induces the clustering and tyrosine phosphorylation of ErbB2, and not of the other ErbB family members, at sites of bacterial adhesion (Hoffmann et al. (2001) *Cell Biol* 155:133-43), it was therefore aimed to determine whether the interaction of ErbB2 with ERM proteins might account for the specific recruitment of ErbB2 induced by *N. meningitidis*. First, using a chimeric molecule encompassing the extracellular domain of EGFR fused to the transmembrane and intracellular domains of ErbB-2 (EGFR/ErbB-2 chimera) expressed in endothelial cells, it was observed that, whereas EGFR was not recruited, the EGFR/ErbB-2 chimera, like endogenous ErbB2, was largely accumulated at sites of bacterial adhesion where it co-localised with ezrin. These data demonstrate that the transmembrane and intracellular domains of ErbB2 are sufficient to promote the bacteria-induced clustering of ErbB2.

To determine whether the juxtamembrane ERM binding motif is necessary for *N. meningitidis*-induced ErbB2 recruitment, gD-tagged ErbB2 constructs with C-terminal truncations at residues 676, 684 or 689 were generated and their ability to accumulate at sites of bacterial adhesion was examined when expressed in endothelial cells. It was shown that recruitment of Δ689 truncated ErbB2, which contains the ERM binding motif, was equivalent to recruitment of the full length receptor by *N. meningitidis*. However, recruitment at sites of *N. meningitidis* adhesion of both Δ684 and Δ676 proteins with partial or complete truncation of the ERM binding motif was defective. In addition, when expressed in endothelial cells, the ErbB2-ΔEBM construct was also poorly accumulated at bacterial adhesion sites, therefore demonstrating that the ERM binding motif of ErbB2 is necessary to promote ErbB2 localisation within microvillus-like structures induced by *N. meningitidis* adhesion to human endothelial cells. In contrast, mutations within the ezrin binding motif did not affect cellular localisation of ErbB2 within EGF-induced lamellipodia.

In epithelia, ErbB2 is predominantly localised at the basolateral membrane by interactions of its carboxy-terminal motif with PDZ domain-containing proteins (Borg et al (2000) *Nat Cell Biol* 2:407-14, Shelly et al. (2003) *Dev Cell* 5:475-86). In addition, a bipartite sorting signal, located between amino acid 692 and 701 next to the ERM binding motif, is also necessary to ensure the proper targeting of ErbB2 to the basolateral membrane (Dillon et al. (2002) *Mol Cell Biol* 22:6553-63). However, the mechanism by which a minor population of ErbB2 reaches the apical surface remains unsolved. The question was therefore addressed whether ErbB2 interaction with ERM proteins might be required for ErbB2 targeting to the epithelial apical cell surface. To explore this hypothesis, advantage was taken of the LLC-PK1 epithelial cell line, as these cells, which retain many features of kidney proximal tubule epithelial cells have numerous microvilli at the apical surface, the formation of which requires the conformational activation of ERM proteins (Gautreau et al. (2000) *Cell Biol* 150:193-203, Fievet et al. (2004) *J Cell Biol* 164:653-9). In addition, LLC-PK1 cells are deficient in the μ1B subunit of the AP1B adaptor complex, and significant amounts of ErbB2 are missorted to the apical membrane. Both wild-type and mutated forms of gD-tagged ErbB2 were expressed in LLC-PK1 epithelial cells. As expected for polarised epithelial cells, E-cadherin and b-catenin were distributed on the lateral membranes with additional weak staining of the basement membrane, the zona occludens protein ZO-1 was detected in the tight junctions at the interface between the apical and basolateral domains and ezrin was mainly localised at the apical microvilli with additional faint signal at cell-cell contacts. In agreement with previous reports, it was found that wild-type ErbB2 was predominantly localised at the basolateral membrane, underneath ZO-1 staining. In addition, a significant fraction of ErbB2 was present at the apical membrane that co-localised with ezrin within apical microvilli. However, mutations in the ezrin binding domain of ErbB2, which did not affect ErbB2 targeting to the basolateral membrane, totally abolished its localisation at the apical surface within ezrin-enriched microvilli structures.

Taken together, these results demonstrate that ErbB2 interaction with ERM proteins can control the cellular localisation of ErbB2 within microvilli structures.

Example 3

ERM Proteins Control ErbB2 Activation

It was observed that ezrin and moesin can interact through their FERM domain with the juxtamembrane domain of ErbB2. Interestingly, while performing pull-down experiments, it was noticed that only the non-phosphorylated form of either endogenous or gD-tagged ErbB2 were pulled down with the ezrin FERM domain, as no signal was detected using an anti-phosphotyrosine antibody. In addition, it was unexpectedly observed that activation of ErbB2 induced by infection with *N. meningitidis* was accompanied by the dissociation of the complexes formed between ErbB2 and both ezrin and moesin. Similarly, EGF-induced activation of ErbB2 was accompanied by a large reduction of the interaction between ErbB2 and both ezrin and moesin. Moreover, overexpression of wild-type ErbB2 in human endothelial cells displays the characteristic phosphorylation pattern indicative of constitutive ErbB2 activation. However, it was observed that while ezrin was detected in immunoprecipitates of non-activated endogenous ErbB2, it was poorly detected in immunoprecipitates of overexpressed ErbB2, therefore further confirming that ERM proteins only interact with non-phoshorylated ErbB2. Conversely, it was unexpectedly observed that the mutated form of ErbB2 was constitutively phosphorylated to a greater degree than wild-type, therefore indicating that mutagenesis within the ERM binding domain of ErbB2, which disrupts the ErbB2-ezrin interaction, potentiated receptor phosphorylation. All together, these results strongly suggested that interaction of ERM proteins with the non-activated form of ErbB2 might control receptor activation.

To test this hypothesis, it was therefore examined whether expression of ERM proteins could reverse the activation of ErbB2. For this, wild-type ErbB2 was overexpressed in human endothelial cells, alone or in combination with ERM mutants either mimicking phosphorylated form (threonine to aspartic acid mutation, T567D in ezrin) or non-phosphorylated form (threonine to alanine mutation, T567A in ezrin), as it was previously described that T567D mutation bypasses the need for PIP2 binding to unmask both membrane and actin binding sites, whereas T567A remains inactive (Gautreau et al. (2000) *J Cell Biol* 150:193-203, Fievet et al. (2004) *J Cell Biol* 164:653-9). Interestingly, it was observed that, whereas expression of the T567A mutant of ezrin had no effect, the phosphorylation state of overexpressed ErbB2 was reduced by 60% when ErbB2 was co-expressed with the active open form of ezrin (ezrin-T567D) (FIG. 3). Additionally, expression of the PERM domain of ezrin on its own was also sufficient to reduce the tyrosine phosphorylation of overexpressed ErbB2 by 50 to 60% (FIG. 3). As expected, inhibition of the tyrosine phosphorylation of ErbB2 promoted by both the T567D mutant and the FERM domain of ezrin was accompanied by a large reduction in the activation of the mitogen-activated protein kinase (MAPK) Erk1/2 and AKT, the two main pathways coupled to ErbB2 activation, as assessed using phospho-specific antibodies directed against active forms of both MAPK-Erk1/2 (Thr202/Tyr204) and AKT (Ser473/Thr308) (FIG. 4). However, consistent with the data presented above, expression of the ezrin FERM domain had no effect on the activation of the form of ErbB2 mutated in the ERM binding domain.

The question was therefore addressed whether the inhibition exerted by the expression of the FERM domain would result in decreased cell proliferation, known to be dependent upon ErbB2-induced AKT activation (Junttila et al. (2009) *Cancer Cell* 15:429-40). For this, both the wild-type and ΔEBM forms of ErbB2 were expressed in human endothelial cells, alone or in combination with the ezrin FERM domain, and cell proliferation was monitored. It was shown expression of wild-type ErbB2 induced a 2.5 to 3 fold increase in cell proliferation detectable within 48 h of cell transfection, and that co-expression of the ezrin FERM domain reduced this ErbB2-induced cell proliferation by 70 to 85% (FIG. 5). In contrast, expression of the FERM domain had no effect on cell proliferation induced by the expression of ErbB2 ΔEBM, nor on the basal proliferation level of endothelial cells. Altogether these results demonstrate that interaction of the juxtamembrane domain of ErbB2 with the ERM proteins prevents the activation of overexpressed ErbB2, while loss of this interaction contributes to ErbB2 activation.

Example 4

ERM Proteins Specifically Prevent the Ligand-Independent Activation of ErbB2

As expression of open forms of ezrin could prevent the ligand-independent activation characteristic of ErbB2 overexpression, it was next investigated whether these open forms could inhibit the ligand-independent activation of ErbB2 that results from mutations in the ErbB2 transmembrane domain (the neu oncogenic form, valine 659 replaced with glutamate in human ErbB2). Interestingly, ErbB2-V659E phosphorylation and downstream activation of AKT promoted by expression of this mutated oncogenic form were also reduced by 60% when coexpressed with the ezrin FERM domain or the T567D mutant. These results provide additional evidence that the interaction between ERM proteins and ErbB2 plays a critical role in the control of the ligand-independent activation of ErbB2.

Because ErbB2 can be activated by both ligand-independent and -dependent mechanisms, it was also investigated whether expression of open forms of ezrin could regulate its ligand-dependent activation in heterodimers with the other family members. It was shown that EGF stimulation of human endothelial cells induced the formation of activated complexes between endogenous ErbB2 and EGFR and the downstream activation of both MAPK-Erk1/2 and AKT pathways (FIG. 6). Endothelial response to EGF stimulation was not affected by expression of the ezrin FERM domain. In addition, the endothelial response to Heregulin-1β (HRG) treatment was assessed, which is known to be critically dependent upon the formation of ErbB2-ErbB3 complexes, as ErbB3, which is enzymatically inactive, is required for ligand association and active ErbB2 tyrosine kinase to initiate the activation of a phosphatidylinositol 3-kinase/AKT pathway (Pin kas-Kramarski et al. (1996) *Embo J* 15:2452-67, Holbro et al. (2003) *Proc Natl Acad Sci USA* 100:8933-8). Using immunoprecipitation methods, no endogenous activated ErbB2/ErbB3 complexes induced by HRG stimulation were detected, most likely due to the scarce formation of such complexes. However, it was observed that HRG-induced activation of AKT was not affected by expression of either the T567D mutant or the FERM domain of ezrin, therefore indicating that, as observed for EGF-induced activation of ErbB2 in heterodimers with EGFR, open active forms of ezrin did not affect HRG-induced activation of ErbB2 in heterodimers with ErbB3. All together these results indicate that ERM protein interaction with ErbB2 specifically prevents the ligand-independent activation of ErbB2.

Example 5

ERM Proteins Stabilise ErbB2 in a Catalytically Repressed State

To further explore how ERM interaction with the juxtamembrane domain of ErbB2 controls the ligand-independent activation state of ErbB2, it was investigated whether this interaction could prevent ErbB2 self-association. ErbB2 dimerisation was assessed as previously described (Penuel et al. (2002) *J Biol Chem* 277:28468-73), using $BS^3$, a non-cleavable, membrane-impermeable crosslinking agent, prior to cell lysis, immunoprecipitation and analysis by western blot. Cross-linking studies demonstrated that when ErbB2 was overexpressed in the presence of GFP alone, self association was accompanied by the tyrosine-phosphorylation of ErbB2 (FIG. 7). Consistent with a previous study, substitution of a short amino acid sequence within the cytosolic domain, VVI (residues 966-968) with alanines, which abrogates ErbB2 association, prevented ErbB2 phosphorylation. However, surprisingly, it was observed that while expression of the VSV-g-tagged ezrin mutant T567D or the VSV-g-FERM domain of ezrin decreased ErbB2 tyrosine phosphorylation by 50 to 60%, this effect was not accompanied by alteration in the ability of ErbB2 to self-associate, as the total quantities of ErbB2 molecules stabilised in oligomeric forms by $BS^3$ treatment were similar (FIG. 7). Similarly to the observations made using wild-type ErbB2, co-expression of the VSV-g-ezrin FERM domain together with the ErbB2-V659E mutant reduced the tyrosine phosphorylation of this ErbB2 mutant by 60 to 65%, but did not affect the ability of this oncogenic form to self-associate. In addition, as expected, co-expression of the VSV-g-ezrin FERM domain did not affect the ability of the ErbB2-DERM mutant to form tyrosine phosphorylated oligomers. These results indicate that ErbB2 interaction with open forms of ezrin inhibits ErbB2 activation without affecting the formation of ErbB2 dimers. These results strongly suggest that ERM proteins stabilise ErbB2 in a catalytically repressed state by exerting a negative molecular constraint on the juxtamembrane domain of ErbB2, restricting access of the kinase domain to substrate tyrosines.

Interestingly, it was observed that while expression of a VSV-g-tagged FERM domain of ezrin did not affect ErbB2 dimerisation, expression of the FERM domain of ezrin coupled to GFP (FERM-GFP) completely abrogated the ability of ErbB2 to self-associate and to induce ErbB2 tyrosine phosphorylation (FIG. 7), as observed with VVI/AAA mutation in ErbB2, which abrogates ErbB2 association. Expression of FERM-GFP also more efficiently reversed the ligand-independent activation of ErbB2, as both receptor activation and downstream activation of MAPK-Erk1/2 and AKT due to overexpressed ErbB2 and ErbB2-V659E mutant were strongly and dose-dependently inhibited by 60 to 100% when co-expressed in the presence of FERM-GFP. These results provide additional evidence that interaction of ERM proteins with ErbB2 exerts molecular constraint on the juxtamembrane domain of ErbB2, which could further lead to the disruption of ErbB2 self association, when the ezrin FERM domain is exogenously coupled to GFP, most likely due to an additional allosteric effect exerted by the presence of the GFP molecule.

To further explore how interaction of ERM proteins with ErbB2 exerts a negative allosteric effect exclusively in the context of the ligand-independent activation of ErbB2, it was next addressed whether the conformation of the extracellular domain could impact the effect exerted by ERM proteins. Indeed, structural studies indicate that ectodomain transition to the ligand-bound, active conformation is relayed across the plasma membrane inducing conformational changes that relieve intramolecular constraints imposed on the kinase domain (Linggi et al (2006) *Trends Cell Biol* 16: 649-56). To address this question, the chimeric molecule were utilized, which encompass the extracellular domain of EGFR fused to the transmembrane and intracellular domains of ErbB2, as ErbB2 kinase activity in this EGFR/ErbB-2 chimera is now regulated by EGF binding (Lee et al. (1989) *Embo J* 8:167-73). Of particular interest, it was observed that expression of GFP-FERM domain of ezrin had no effect on the ligand-induced activation of the chimeric molecule. These data demonstrate that the specific activity of ERM proteins on the ligand-independent activation of ErbB2 not only relies on the ERM binding motif present in the juxtamembrane domain of ErbB2, but is also dependent on the conformation adopted by the extracellular domain.

Altogether, these data provide evidence that the ligand-independent activation of ErbB2 is suppressed by ERM protein interaction with the juxtamembrane region of ErbB2, which stabilises the amino-terminal kinase lobe in an inactive state. In contrast, ligand-stimulated oligomerisation of ErbB2 prevents the inhibitory effect exerted by ERM proteins, most likely by destabilising the inhibitory conformation of the juxtamembrane region.

Example 6

ERM Proteins can Prevent ErbB2 Activation in ErbB2-Overexpressing Tumour Cells

The data revealed that ERM proteins can control the ligand-independent activation of ErbB2. Therefore it was investigated whether alteration of the ratio between ErbB2/ERM proteins, due to ErbB2 overexpression, could contribute to the constitutive activation of ErbB2 in breast cancer cells. The level of expression of these proteins was assessed in two breast cancer cell lines, SKBR-3 and BT474, which exhibit ErbB2 gene amplification. It was observed that these two cell lines expressed ezrin at level similar to that observed in non tumour cells, but not moesin. It was therefore analysed the effect exerted by increasing the quantity of ERM proteins on the constitutive activation of ErbB2 in breast cancer cells. It was observed that expression of the VSV-g-tagged FERM domain in SKBR-3 cells caused a strong and dose-dependent decrease in both ErbB2 phosphorylation and downstream activation of AKT and ErK1/2 (60%-45%) (FIG. 8). In cancer cells, inhibition of ErbB2 phosphorylation or activation of downstream signalling events was also observed with the expression of the full length form of ezrin. These results, which demonstrate that expression of an active open form of ezrin reverse ErbB2 activation in a context of tumour cells exhibiting ErbB2 amplification, further confirm that ERM proteins are key molecules controlling the activation status of ErbB2. In addition, these data indicate that the effect exerted by expression of the ezrin FERM domain on the ligand-independent activation of ErbB2 could be used to efficiently prevent ErbB2 activation in cancer cell lines expressing high levels of ErbB2.

Since it was observed that coupling GFP to ezrin or to the FERM domain further contributed to the inhibition of ErbB2 activation by disrupting ErbB2 self association, the effect of these constructs was assessed on the activation status of ErbB2 in SKBR3 and BT474 breast cancer cell lines. As expected, expression of ezrin-GFP and more effectively FERM-GFP drastically inhibited the activation of ErbB2 and downstream signalling pathways in both SKBR3 (FIG. 9) and BT474 (FIG. 10), therefore indicating that disruption of ErbB2 self assembly promoted by the chimeric molecule provides a valuable gain in preventing ErbB2 activation in tumor cell lines overexpressing ErbB2.

Altogether, these results bring to light a new function for ERM proteins as gate keepers, preventing ligand-independent activation of ErbB2 and suggest a mechanism for abnormal receptor activation in tumour cells overexpressing ErbB2. In the light of these findings, the delivery of a functional FERM domain of ezrin into living cells appears to be a promising strategy for the treatment of ErbB2-dependent breast cancers.

Example 7

Expression and Purification of FERM-Zebra Fusion Protein

The vectorization method used takes advantage of the transduction properties of the Epstein-Barr virus transcription factor Zebra. This factor allows a very efficient transduction of large molecules (GFP, alpha-galactosidase) in the cytoplasm of cells including breast tumor cells SKBR3 and BT474, without any toxic effect and without affecting the function of the reporter gene.

The FERM domain was fused in different ways to the Zebra protein of Epstein-Barr virus and with a 6 histidine tag which allows the protein purification on a Ni column (FIG. 11). The ezrin FERM domain was coupled to the Zebra protein by its amino (Zebra-FERM) or carboxy-terminal (FERM-Zebra) end. As the fusion of a tag to the amino-terminal end of the ezrin FERM domain may affect its properties, the Zebra-FERM constructs may thus be used as negative controls in all the tests. The GFP protein fused to the Zebra protein (Zebra-GFP) is used as negative control.

The results obtained by immunofluorescence and flow cytometry show that the Zebra-GFP protein penetrates efficiently and in a dose-dependent manner in the HBMECs endothelial cells, as well as in the tumor cells SKBR3 and BT474 and that it remains in the cells for up to 48 hours. The transduction is more efficient when the transduction medium has not been withdrawn (addition of complete medium without washes). These experimental conditions were thus used for all the transductions of protein fusions.

Example 8

FERM-Zebra Protein Transduction Inhibits ErbB2 Activity and the Proliferation of Tumor Cells The ability of the fusion protein FERM-Zebra to inhibit activation of ErbB2 and of the signaling pathways coupled to ErbB2 was tested in SKBR3 cells. The results obtained show that the protein is properly transduced within the cells and that the FERM domain thus introduced remains functional, since it inhibits the ErbB2 tyrosine phosphorylation in a dose dependent manner (FIG. 12). This effect is observed 24 hours after transduction.

A study of the in vitro effect of the transduction of the vectorized FERM domain on the SKBR3 tumor cells proliferation was also carried out (FIG. 13). The transduction of the FERM-Zebra construct inhibits proliferation of SKBR3 tumor cells over two days, as compared with the controls: buffer containing DTT (present in the dialysis buffer) or with the Zebra-GFP construct (FIG. 14). The transduction of the FERM domain inhibits the activation of ErbB2 and the activation downstream of AKT.

The invention claimed is:

1. A method of inhibiting ErbB2-induced cell proliferation in an individual having an ErbB2-dependent cancer, by inhibiting the ligand-independent activation of ErbB2 in the cells of said individual, comprising administering to said individual a pharmaceutical composition comprising:

a polypeptide selected from the group consisting of the FERM domain of an ERM protein, an ERM protein mutant and a fragment thereof provided that said ERM protein mutant and said fragments are able to inhibit the ligand-independent activation of ErbB2 in cells, or at least one nucleic acid encoding said polypeptide, wherein said polypeptide comprises at least one polypeptide selected from the group consisting of SEQ ID NO:1, SEQ ID NO:2, SEQ ID NO:3 and SEQ ID NO:4.

2. A method of inhibiting ErbB2-induced cell proliferation in an individual having an ErbB2-dependent cancer, by inhibiting the ligand-independent activation of ErbB2 in the cells of said individual, comprising administering to said individual a pharmaceutical composition comprising:

a fusion polypeptide comprising a polypeptide selected from the group consisting of the FERM domain of an ERM protein, an ERM protein mutant, and a fragment thereof provided that said ERM protein mutant and said fragment are able to inhibit the ligand-independent activation of ErbB2 in cells, or at least one nucleic acid fully encoding the fusion polypeptide, wherein said fusion polypeptide comprises at least one polypeptide selected from the group consisting of SEQ ID NO: 1, SEQ ID NO: 2, SEQ ID NO: 3 and SEQ ID NO: 4, which is linked to a second polypeptide selected from the group consisting of a protein transduction domain, a cell penetrating peptide and a cell targeting peptide.

3. The method according to claim 2, wherein said second polypeptide is selected from the group consisting of a Zebra protein transduction domain, a HIV TAT protein transduction domain, penetratin, a V1 or DV3 peptide derived from the viral chemokine vMIP-II and a polyarginine peptide.

4. The method according to claim 2, wherein the fusion polypeptide comprises a polypeptide consisting of SEQ ID NO: 1 linked at its carboxy-terminal end to a Zebra protein transduction domain.

5. The method of claim 1, wherein said ErbB2-dependent cancer is selected from the group consisting of breast cancer, ovarian cancer, colorectal cancer and gastric cancer.

* * * * *